(12) United States Patent
Ivachtchenko et al.

(10) Patent No.: US 8,889,701 B1
(45) Date of Patent: Nov. 18, 2014

(54) SUBSTITUTED (S)-(2R,3R,5R)-3-HYDROXY-(5-PYRIMIDIN-1-YL)TETRAHYDROFURAN-2-YLMETHYL ARYL PHOSPHORAMIDATE

(71) Applicant: Alla Chem, LLC, Carson City, NV (US)

(72) Inventors: Alexandre Vasilievich Ivachtchenko, Encinitas, CA (US); Andrey Alexandrovich Ivashchenko, Moscow (RU); Oleg Dmitrievich Mitkin, Moscow (RU)

( * ) Notice: Subject to any disclaimer, the term of this patent is extended or adjusted under 35 U.S.C. 154(b) by 0 days.

(21) Appl. No.: 14/051,464

(22) Filed: Oct. 11, 2013

(51) Int. Cl.
| | | |
|---|---|---|
| *A01N 43/54* | (2006.01) | |
| *A61K 31/505* | (2006.01) | |
| *A61K 45/06* | (2006.01) | |
| *C07F 9/6558* | (2006.01) | |
| *A61K 31/695* | (2006.01) | |
| *A61K 31/675* | (2006.01) | |

(52) U.S. Cl.
CPC .............. *C07F 9/65586* (2013.01); *A61K 45/06* (2013.01); *A61K 31/695* (2013.01); *A61K 31/675* (2013.01)
USPC ......................................... 514/274; 544/310

(58) Field of Classification Search
CPC ............................ C07D 239/54; A61K 21/513
USPC ........................................... 544/310; 514/274
See application file for complete search history.

(56) References Cited

FOREIGN PATENT DOCUMENTS

WO    WO 2012142075 A1 * 10/2012

* cited by examiner

*Primary Examiner* — James O Wilson
*Assistant Examiner* — Alexander R Pagano

(57) ABSTRACT

The instant invention relates to a novel compound representing a substituted phosphoramidic acid—a (2R,3R,5R)-3-hydroxy-(5-pyrimidin-1-yl)tetrahydrofuran-2-yl)methyl aryl phosphoramidate of formula 1 or a (S)-(2R,3R,5R)-3-hydroxy-(5-pyrimidin-1-yl)tetrahydrofuran-2-yl)methyl aryl phosphoramidate of formula 2, or a pharmaceutically acceptable salt, a hydrate, a crystalline form or a stereoisomer thereof, as defined in the specification.

The novel compound is used for a pharmaceutical composition with at least one pharmaceutically acceptable excipient as well as with an inosine 5 monophosphate dehydrogenase inhibitor, HCV protease NS3 inhibitor, HCV protease NS3/4A inhibitor, and RNA polymerase NS5A inhibitor. The novel compound is useful as a viral polymerase HCV NS5B inhibitor and can be used for treating a disease caused by hepatitis C virus (HCV).

11 Claims, No Drawings

SUBSTITUTED (S)-(2R,3R,5R)-3-HYDROXY-(5-PYRIMIDIN-1-YL)TETRAHYDROFURAN-2-YLMETHYL ARYL PHOSPHORAMIDATE

The present invention relates to novel substituted phosphoramidic acid esters and their use as agent for treating viral diseases. These compounds are inhibitors of RNA-dependent RNA viral replication and are useful as inhibitors of HCV NS5B polymerase, as inhibitors of hepatitis C (HCV) virus replication and for treatment of hepatitis C infection in mammals. Hepatitis C virus, together with the other important human pathogens, such as yellow fever virus, West Nile virus, Dengue virus and hepatitis GBV-C virus, belongs to genus *Flaviviridae*.

It is known that NS5B is a hepatic virus protein [Vincent Soriano et al., Hepatitis C therapy with HCV NS5B polymerase inhibitors, *Expert Opinion on Pharmacotherapy*, June 2013, Vol. 14, No. 9, Pages 1161-1170]. Antiviral drug development for HCV is progressing at a feverish pace. Amongst HCV polymerase inhibitors, sofosbuvir has positioned as unique companion with ribavirin as therapy for most HCV genotypes 2 or 3.

The current treatment of chronic hepatitis C based on the combination of pegylated interferon and ribavirin is effective in only 50% of patients. Specific targeted antiviral therapies represent a promising approach to eradicate the infection. The review [Legrand-Abravanel F, Nicot F, Izopet J. New NS5B polymerase inhibitors for hepatitis C. *Expert Opin Investig Drugs*. 2010 August; 19(8):963-75] focuses on progress towards the development of the hepatitis C virus (HCV) polymerase inhibitors that have entered clinical development in recent years. Nucleos(t)ide analogues target the active site of the HCV polymerase and acts as chain terminators. They have similar activity against all genotypes and the virus has a high genetic barrier to drug resistance. Non-nucleoside inhibitors achieve polymerase inhibition by binding to one of the at least four allosteric enzyme sites. Most of them have a genotype-specific activity and they may select rapidly drug-resistant variants if HCV replication is not completely suppressed. Nonetheless, they provide additional options for addressing the needs of infected patients. NS5B polymerase inhibitors will form an integral part of more effective anti-HCV therapy, in combination with interferon or with other directly acting antiviral agents.

In the past decade, intensive efforts have focused on the discovery of both nucleos(t)ide and non-nucleoside inhibitors of the HCV NS5B polymerase. These efforts have resulted in several promising agents advancing in clinical development. The review [Watkins W J, Ray A S, Chong L S. HCV NS5B polymerase inhibitors. *Curr Opin Drug Discov Devel*. 2010 July; 13(4): 441-65] traces the history of optimization of the chemical series that have led to the development of clinical candidates, and summarizes recent developments in the field, with emphasis on clinical efficacy and impact for future combination studies.

As the examples of drug candidates there may be mentioned nucleoside inhibitors of HCV NS5B polymerase: PSI-7977 ФИрмы Фармасет (США) ИNM283 (Valopicitabine) ФИрмы АИдеНИкс (США) Идр. [M. J. Sofia, D. Bao, W. Chang, J. Du, D. Nagarathnam, S. Rachakonda, P. G. Reddy, B. S. Ross, P. Wang, H.-R. Zhang, S. Bansal, C. Espiritu, M. Keilman, A. M. Lam, H. M. M. Steuer, Congrong Niu, M. J. Otto, P. A. Furman Discovery of a β-D-20-Deoxy-20-r-fluoro-20-β-C-methyluridine Nucleotide Prodrug (PSI-7977) for the Treatment of Hepatitis C Virus. *J. Med. Chem*. 2010, 53, 7202-7218; U.S. Pat. No. 7,964,580 B2; U.S. Pat. No. 8,334,270 B2.].

Up to the present hepatitis C is a serious problem of Healthcare Service. It leads to chronic liver disease, such as cirrhosis and hepatocellular carcinoma.

In this connection searching for novel anti flaviviral therapies of high efficiency is still one of the main tendencies in creation of novel pharmacological agents for treatment of wide and diverse range of viral infections, including HCV. Therefore synthesis of novel compounds and their use as antiviral active ingredients of pharmaceutical compositions and medicaments including HCV is still important.

In context of the invention, terms are generally defined as follows:

"Alkyl" refers to an aliphatic hydrocarbon unbranched or branched chain with 1-12 carbon atoms. Branched means alkyl chain with one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonylheteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k^a R_{k+1}^a N-$, $R_k^a R_{k+1}^a NC(=O)-$, $R_k^a R_{k+1}^a NC(=S)-$, $R_k^a R_{k+1}^a NSO_2-$, where $R_k^a$ and $R_{k+1}^a$ independently of each other represent "amino group substituents" the meanings of which are defined in this section, for example, hydrogen, alkyl, aryl, aralkyl, heteroaralkyl, heterocyclyl or heteroaryl, or $R_k^a$ and $R_{k+1}^a$ together with the N-atom, they are attached to, form through $R_k^a$ and $R_{k+1}^a$ 4-7-membered heterocyclyl or heterocyclenyl. The preferred alkyl groups are methyl, trifluoromethyl, cyclopropylmethyl, cyclopentylmethyl, ethyl, n-propyl, iso-propyl, n-butyl, tent-butyl, n-pentyl, 3-pentyl, methoxyethyl, carboxymethyl, methoxycarbonylmethyl, ethoxycarbonylmethyl, benzyloxycarbonylmethyl and pyridylmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, hetero aralkyloxycarbonyl or $R_k^a R_{k+1}^a N-$, $R_k^a R_{k+1}^a NC(=O)-$, annelated arylheterocyclenyl, annelated arylheterocyclyl.

"Alkyloxy (alkoxy)" refers to a $C_n H_{2n+1}O-$ group, in which alkyl is defined in this section. The preferred alkyloxy groups are methyloxy, ethyloxy, n-propyloxy, iso-propyloxy and n-butoxy.

"Aryl" refers to an aromatic mono- or polycyclic system comprising 6-14 carbon atoms, predominantly 6-10 carbon atoms. Aryl may have one or more "cyclic system substituents" of the same or different structure. Phenyl, substituted phenyl, naphthyl, and substituted naphthyl are the representatives of aryl groups. Aryl can be annelated with nonaromatic cyclic system or heterocycle.

"Aryloxy" refers to an aryl-O— group in which the meaning of aryl is defined in this section. Phenoxy and 2-naphthyloxy- are the representatives of aryloxy groups.

"Hydrate" means stoichiometric or nonstoichiometric compositions of compounds or their salts with water.

"Substituent" means a chemical radical attached to a scaffold (fragment), for example, "alkyl substituent", "amino group substituent", "carbamoyl substituent", and "cyclic system substituent".

"Active component" (drug-substance) refers to a physiologically active compound of synthetic or other (biotechnological, vegetable, animal, microbe and so on) origins exhibiting pharmacological activity which is an active ingredient of pharmaceutical composition employing in production and preparation of medicaments.

"Medicament"—is a compound (or a mixture of compounds as a pharmaceutical composition) in the form of tablets, capsules, injections, ointments and other ready forms intended for restoration, improvement or modification of physiological functions in humans and animals, and for treatment and prophylaxis of diseases, for diagnostics, anesthesia, contraception, cosmetology and others.

"Lower alkyl" refers to an unbranched or branched alkyl chain comprising 1-4 carbon atoms.

"Therapeutic cocktail" represents a simultaneously administered combination of two or more medicaments exhibiting different mechanism of pharmacological action and directed to various biotargets taking part in disease process.

"Pharmaceutical composition" means a composition comprising a compound of the general formula 1 or 2 and at least one of components selected from the group consisting of pharmaceutically acceptable and pharmacologically compatible fillers, solvents, diluents, carriers, auxiliary, distributing and exipients, delivery agents, such as preservatives, stabilizers, fillers, disintegrators, moisteners, emulsifiers, suspending agents, thickeners, sweeteners, flavouring agents, aromatizing agents, antibacterial agents, fungicides, lubricants, and prolonged delivery controllers, choice and suitable proportions of which depend on nature and way of administration and dosage. Examples of suitable suspending agents are ethoxylated isostearyl alcohol, polyoxyethene, sorbitol and sorbitol ether, microcrystalline cellulose, aluminum metahydroxide, bentonite, agar-agar and tragacant and their mixtures as well. Protection against microorganisms can be provided by various antibacterial and antifungal agents, such as, for example, parabens, chlorobutanole, sorbic acid, and similar compounds. Composition may also comprise isotonic agents, such as, for example, sugar, sodium chloride, and similar compounds. Prolonged effect of composition may be achieved by agents slowing down absorption of active ingredient, for example, aluminum monostearate and gelatine. Examples of suitable carriers, solvents, diluents and delivery agents include water, ethanol, polyalcohols and their mixtures, natural oils (such as olive oil) and organic esters (such as ethyl oleate) for injections. Examples of fillers are lactose, milk-sugar, sodium citrate, calcium carbonate, calcium phosphate and the like. Examples of disintegrators and distributors are starch, alginic acid and its salts, and silicates. Examples of suitable lubricants are magnesium stearate, sodium lauryl sulfate, talc and polyethylene glycol of high molecular weight. A pharmaceutical composition for peroral, sublingval, transdermal, intramuscular, intravenous, subcutaneous, local or rectal administration of active ingredient, alone or in combination with another active compound may be administered to humans and animals in standard administration form, or in mixture with traditional pharmaceutical carriers. Suitable standard administration forms include peroral forms such as tablets, gelatin capsules, pills, powders, granules, chewing-gums and peroral solutions or suspensions; sublingval and transbuccal administration forms; aerosols; implants; local, transdermal, subcutaneous, intramuscular, intravenous, intranasal or intraocular forms and rectal administration forms.

"Pharmaceutically acceptable salt" means relatively nontoxic both organic and inorganic salts of acids and bases disclosed in this invention. The salts could be prepared in situ in the processes of synthesis, isolation or purification of compounds or they could be prepared specially. In particular, salts of bases could be prepared from purified base of the disclosed compound and suitable organic or mineral acid. Examples of salts prepared in this manner include hydrochlorides, hydrobromides, sulfates, bisulfates, phosphates, nitrates, acetates, oxalates, valeriates, oleates, palmitates, stearates, laurates, borates, benzoates, lactates, p-toluenesulfonates, citrates, maleates, fumarates, succinates, tartrates, methane sulphonates, malonates, salicylates, propionates, ethane sulphonates, benzene sulfonates, sulfamates and the like (Detailed description of such salts properties is given in: Berge S. M., et al., "Pharmaceutical Salts" J. Pharm. Sci., 1977, 66: 1-19). Salts of the disclosed acids may also be prepared by the reaction of purified acids with suitable base; moreover, metal salts and amine salts may be synthesized too. Metal salts are salts of sodium, potassium, calcium, barium, zinc, magnesium, lithium and aluminum; sodium and potassium salts being preferred. Suitable inorganic bases from which metal salts can be prepared are sodium hydroxide, carbonate, bicarbonate and hydride; potassium hydroxide, carbonate and bicarbonate, lithium hydroxide, calcium hydroxide, magnesium hydroxide, zinc hydroxide. Organic bases suitable for preparation of the disclosed acid salts are amines and amino acids of sufficient basicity to produce stable salt suitable for medical purposes use (in particular, they are to have low toxicity). Such amines are ammonia, methylamine, dimethylamine, trimethylamine, ethylamine, diethylamine, triethylamine, benzylamine, dibenzylamine, dicyclohexylamine, piperazine, ethylpiperidine, tris(hydroxymethyl)aminomethane and the like. Besides, salts can be prepared using some tetraalkylammonium hydroxides, such as holine, tetramethylammonium, tetraethylammonium, and the like. Aminoacids may be selected from the main aminoacids-lysine, ornithine and agrinine.

One embodiment of the present invention is a novel substituted phosphoramidic acid—a (2R,3R,5R)-3-hydroxy-(5-pyrimidin-1-yl)tetrahydrofuran-2-yl)methyl aryl phosphoramidate of formula 1 or a (5)-(2R,3R,5R)-3-hydroxy-(5-pyrimidin-1-yl)tetrahydrofuran-2-yl)methyl aryl phosphoramidate of formula 2, or a pharmaceutically acceptable salt, a hydrate, a crystalline form or a stereoisomer thereof,

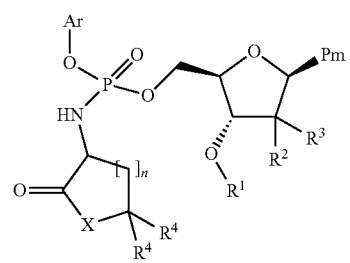

1

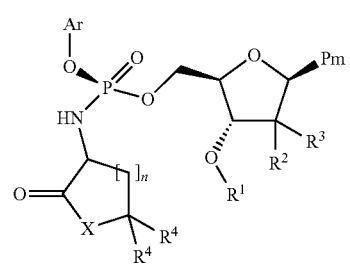

2 wherein:

R¹ is (i) hydrogen, $(CH_3)_2[(CH_3)_3C]Si$, a $C_2$-$C_6$acyl, optionally substituted with $NR^5R^6$ group, wherein $R^5$ and $R^6$ are independently hydrogen or a $C_1$-$C_4$ alkyl; (ii) 1-pyrrole-2-ylcarbonyl, piperidin-3-ylcarbonyl or piperidin-4-ylcarbonyl;

R² and R³ are F; or R³ is $CH_3$ and R² is F or OH;

R⁴ is hydrogen or methyl;

Ar is a phenyl, a pyridyl or a naphthyl, wherein phenyl, pyridyl or naphthyl are optionally substituted with at least one of $C_{1-3}$ alkyl, $C_{2-4}$ alkenyl, $C_{2-4}$ alkynyl, $C_{1-3}$ alkoxy, F, Cl, Br, I, nitro, cyano, —$N(C_{1-3}$ alkyl$)_2$;

Pm is 2,4-dioxo-3,4-dihydro-2H-pyrimidin-1-yl or 4-(4-amino-2-oxo-2H-pyrimidin-1-yl), in which amino group is optionally substituted with 1-pyrrole-2-ylcarbonyl, piperidin-3-ylcarbonyl, piperidin-4-ylcarbonyl or radical $C(O)R^8$, wherein R⁸ is (i) a $C_1$-$C_4$alkyl, optionally substituted with $NR^6R^7$ group, wherein R⁶ and R⁷ are independently hydrogen or $C_1$-$C_4$ alkyl; (ii) a $C_{1-3}$ alkoxy optionally substituted with a phenyl;

X is O or N—R⁹, wherein R⁹ is a $C_1$-$C_4$alkyl, optionally substituted with OH or $OCH_3$;

n=1, 2 or 3.

According to the invention another embodiment is a substituted phosphoramidic acid of formula 1.1 or formula 2.1, or a pharmaceutically acceptable salt, a hydrate, a crystalline form or a stereoisomer thereof,

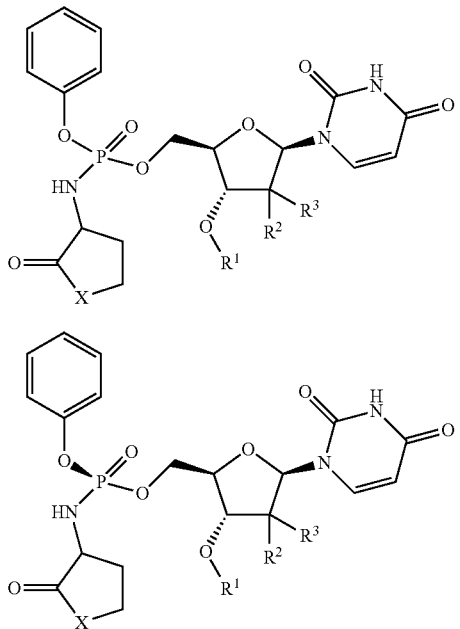

1.1

2.1 wherein R¹, R², R³, and X are as defined herein above.

According to the invention another embodiment provides a preferred derivative of a substituted phosphoramidic acid of formula 1.2 or formula 2.2, or a pharmaceutically acceptable salt, a hydrate, a crystalline form or a stereoisomer thereof,

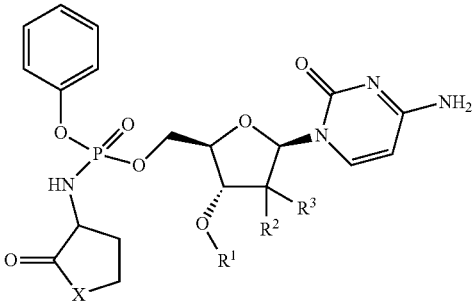

1.2

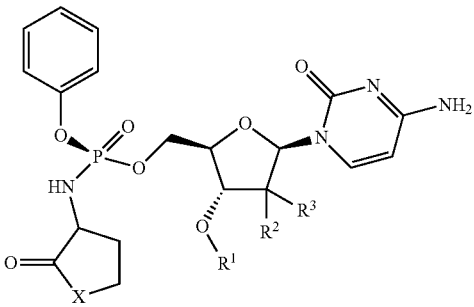

2.2 wherein R¹, R², R³, and X are as defined herein above.

According to the invention the best embodiment is a compound selected from the group consisting of:

((2R,3R,5R)-5-(4-amino-2-oxopyrimidin-1(2H)-yl)-4,4-difluoro-3-hydroxytetrahydrofuran-2-yl)methyl p-tolyl (S)-2-oxo-tetrahydrofuran-3-yl-phosphoramidate 1(1), ((2R,3R,5R)-5-(4-amino-2-oxopyrimidin-1(2H)-yl)-4,4-difluoro-3-hydroxytetrahydrofuran-2-yl)methyl 4-chlorophenyl (S)-2-oxo-tetrahydrofuran-3-yl-phosphoramidate 1(2), ((2R,3R,5R)-5-(4-amino-2-oxopyrimidin-1(2H)-yl)-4,4-difluoro-3-hydroxytetrahydrofuran-2-yl)methyl 2,4-dichlorophenyl (S)-2-oxo-tetrahydrofuran-3-yl-phosphoramidate 1(3), (2R,3R,5R)-5-(4-acetamido-2-oxopyrimidin-1(2H)-yl)-4,4-difluoro-2-(((S)—((S)-2-oxotetrahydrofuran-3-ylamino)(phenoxy)phosphoryloxy)methyl)tetrahydrofuran-3-yl acetate 1(4), benzyl 1-((2R,4R,5R)-4-(benzyloxycarbonyloxy)-3,3-difluoro-5-(((S)—((S)-(2-oxotetrahydrofuran-3-ylamino)(phenoxy)phosphoryloxy)methyl)tetrahydrofuran-2-yl)-2-oxo-1,2-dihydropyrimidin-4-ylcarbamate 1(5), benzyl 1-((2R,4R,5R)-4-(benzyloxycarbonyloxy)-3,3-difluoro-5-(((1-methyl-2-oxopyrrolidin-3-ylamino)(phenoxy)phosphoryloxy)methyl)tetrahydrofuran-2-yl)-2-oxo-1,2-dihydropyrimidin-4-ylcarbamate 1(6), benzyl 1-((2R,4R,5R)-4-(benzyloxycarbonyloxy)-3,3-difluoro-5-(((1-methyl-2-oxopiperidin-3-ylamino)(phenoxy)phosphoryloxy)methyl)tetrahydrofuran-2-yl)-2-oxo-1,2-dihydropyrimidin-4-ylcarbamate 1(7), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopiperidin-3-ylphosphoramidate 1(8), ((2R,3R,5R)-5-(4-amino-2-oxopyrimidin-1(2H)-yl)-4,4-difluoro-3-hydroxytetrahydrofuran-2-yl)methyl phenyl 2-oxooxepan-3-ylphosphoramidate 1(9), benzyl 1-((2R,4R,5R)-4-(benzyloxycarbonyloxy)-5-(((5,5-dimethyl-2-oxotetrahydrofuran-3-ylamino)(phenoxy)

phosphoryloxy)methyl)-3,3-difluorotetrahydrofuran-2-yl)-2-oxo-1,2-dihydropyrimidin-4-ylcarbamate 1(10), ((2R,3R,5R)-5-(2,4-dioxo-3,4-dihydropyrimidin-1(2H)-yl)-4,4-difluoro-3-hydroxytetrahydrofuran-2-yl)methyl phenyl 5,5-dimethyl-2-oxotetrahydrofuran-3-ylphosphoramidate 1(11), (R)-((2R,3R,5R)-5-(2,4-dioxo-3,4-dihydropyrimidin-1(2H)-yl)-4,4-difluoro-3-hydroxytetrahydrofuran-2-yl) methyl phenyl methyl ((S)-2-oxotetrahydrofuran-3-yl)phosphoramidate 1(12), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-yl-phosphoramidate 1(13), ((2R,3R,5R)-5-(4-amino-2-oxopyrimidin-1(2H)-yl)-4,4-difluoro-3-hydroxytetrahydrofuran-2-yl)methyl phenyl 5,5-dimethyl-2-oxotetrahydrofuran-3-yl-phosphoramidate 1(14), (R)-((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 1(15), ((2R,3R,5R)-5-(2,4-dioxo-3,4-dihydropyrimidin-1(2H)-yl)-4,4-difluoro-3-hydroxytetrahydrofuran-2-yl)methyl phenyl 2-oxotetrahydrofuran-3-ylphosphoramidate 1.1(1), ((2R,3R,4R,5R)-5-(2,4-dioxo-3,4-dihydropyrimidin-1(2H)-yl)-4-fluoro-3-hydroxy-4-methyltetrahydrofuran-2-yl)methyl phenyl (S)-2-oxotetrahydrofuran-3-ylphosphoramidate 1.1(2), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 1.1(3), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopyrrolidin-3-ylphosphoramidate 1.1(4), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopiperidin-3-ylphosphoramidate 1.1(5), ((2R,3R,5R)-5-(2,4-dioxo-3,4-dihydropyrimidin-1(2H)-yl)-4,4-difluoro-3-hydroxy-tetrahydrofuran-2-yl)methyl phenyl (R)-2-oxo-tetrahydrofuran-3-ylphosphoramidate 1.1(6), (2R,3R,5R)-5-(4-amino-2-oxopyrimidin-1(2H)-yl)-4,4-difluoro-3-hydroxytetrahydrofuran-2-yl)methyl phenyl (S)-2-oxotetrahydrofuran-3-ylphosphoramidate 1.2(1), (2R,3R,5R)-5-(4-amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2), ((2R,3R,5R)-5-(4-amino-2-oxopyrimidin-1(2H)-yl)-3-(tert-butyldimethylsilyloxy)-4,4-difluorotetrahydrofuran-2-yl)methyl phenyl (S)-2-oxotetrahydrofuran-3-ylphosphoramidate 1.2(3), ((2R,3R,4R,5R)-5-(4-amino-2-oxopyrimidin-1(2H)-yl)-4-fluoro-3-hydroxy-4-methyltetrahydrofuran-2-yl)methyl phenyl (S)-2-oxotetrahydrofuran-3-ylphosphoramidate 1.2(4), ((2R,3R,4R,5R)-5-(4-amino-2-oxopyrimidin-1(2H)-yl)-4-fluoro-3-hydroxy-4-methyltetrahydrofuran-2-yl)methyl phenyl 5,5-dimethyl-2-oxotetrahydrofuran-3-ylphosphoramidate 1.2(5), ((2R,3R,4R,5R)-5-(4-amino-2-oxopyrimidin-1(2H)-yl)-4-fluoro-3-hydroxy-4-methyltetrahydrofuran-2-yl)methyl phenyl 1-methyl-2-oxopyrrolidin-3-ylphosphoramidate 1.2(6), (S)-((2R,3R,5R)-5-(2,4-dioxo-3,4-dihydropyrimidin-1(2H)-yl)-4,4-difluoro-3-hydroxytetrahydrofuran-2-yl)methyl phenyl ((R)-2-oxotetrahydrofuran-3-yl)phosphoramidate 2.1(1), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 2.1(2), and (S)-(2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 2.2(1).

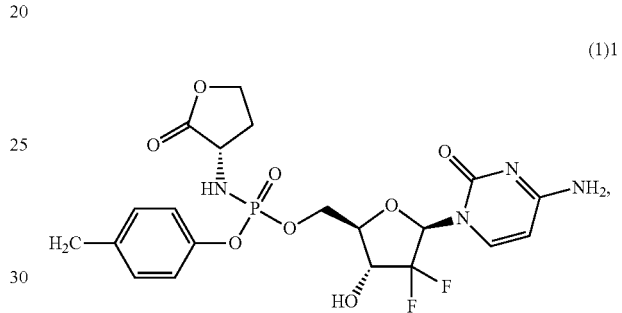

(1)1

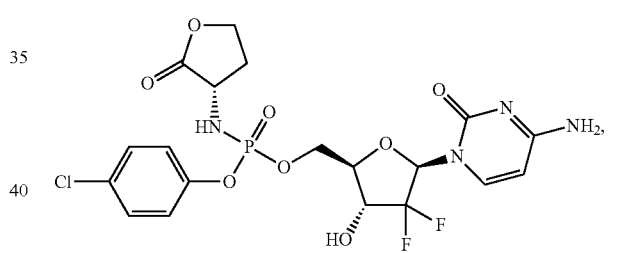

1(2)

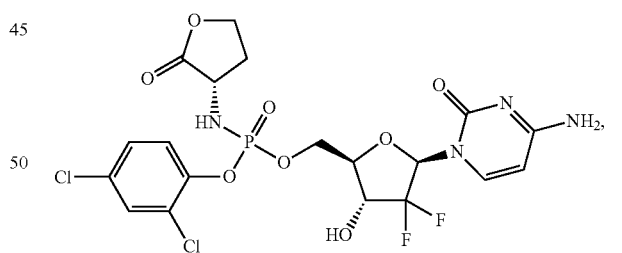

1(3)

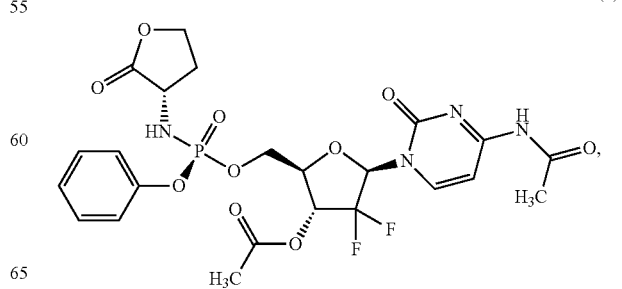

1(4)

1(5)
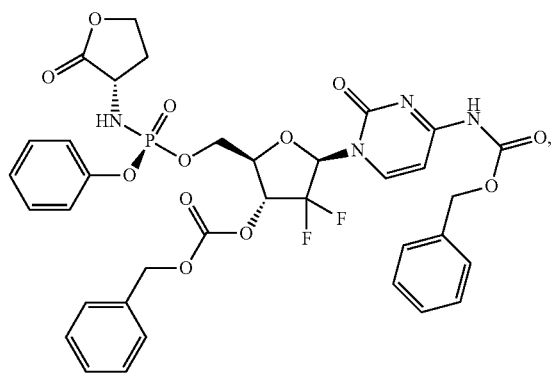
1(6)
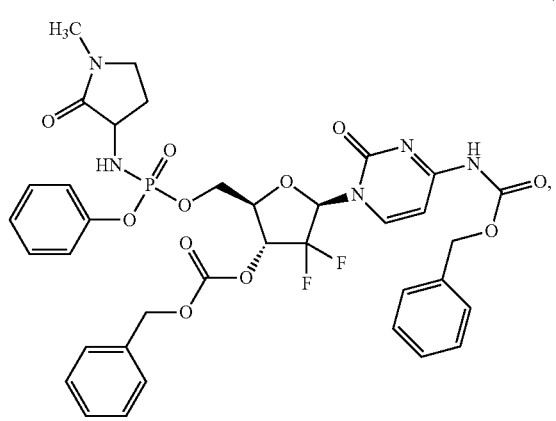
1(7)
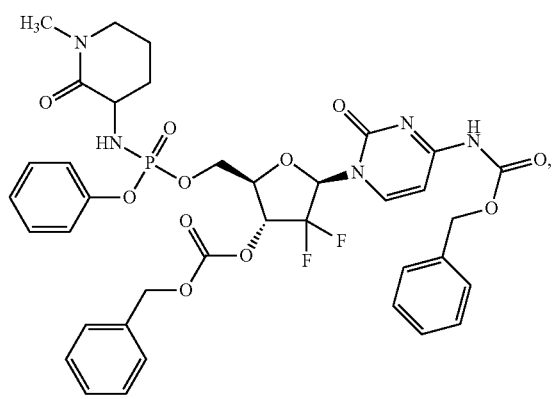
1(8)
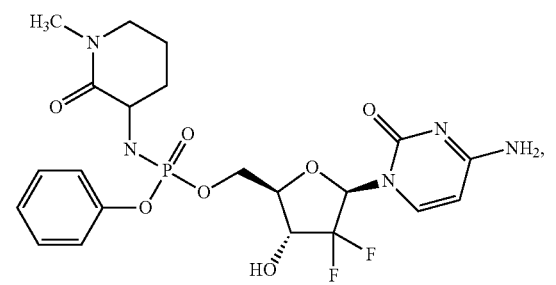
1(9)
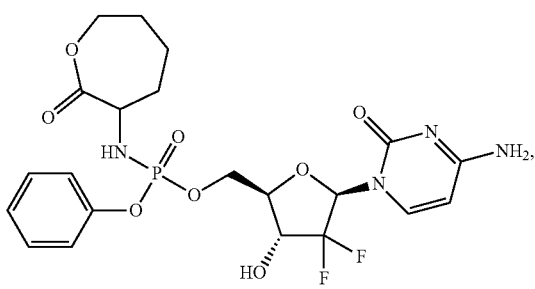
1(10)
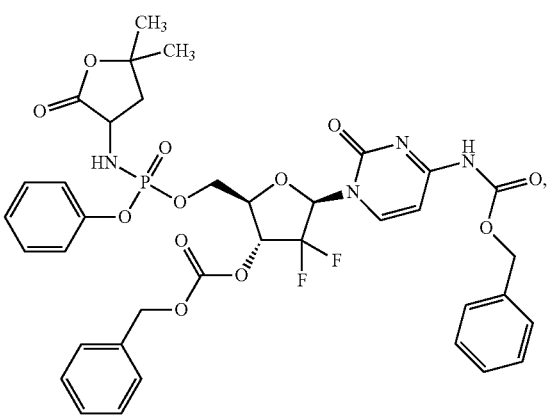
1(11)
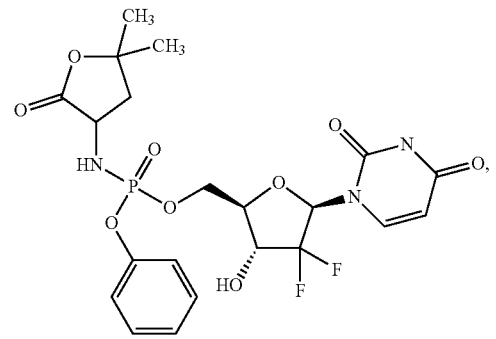
1(12)
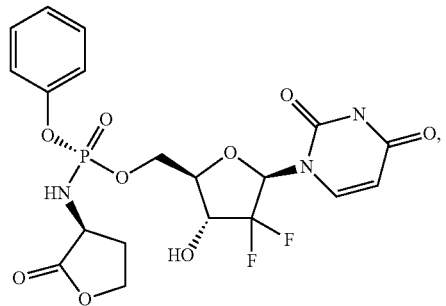

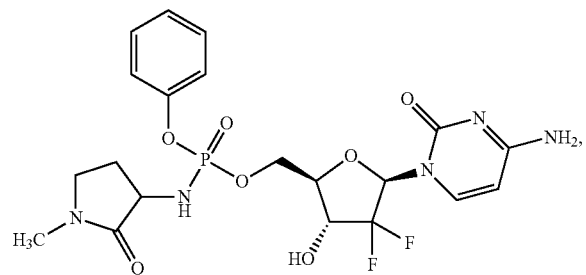
1(13)
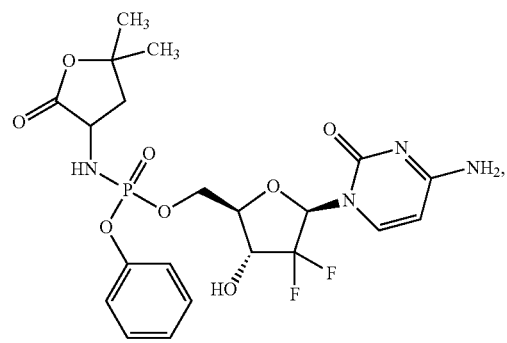
1(14)
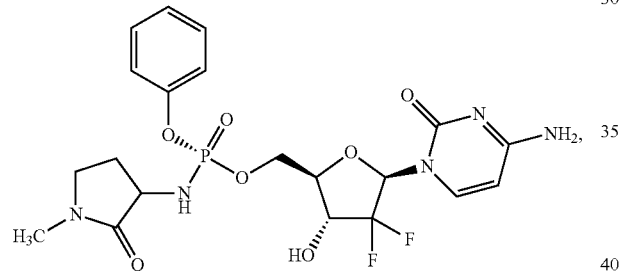
1(15)
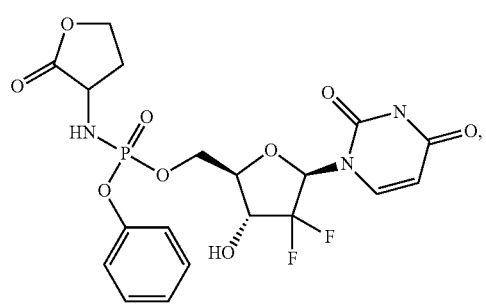
1.1(1)
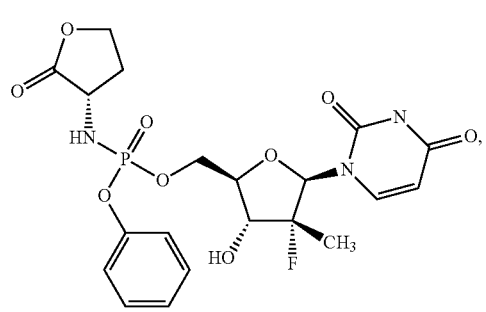
1.1(2)
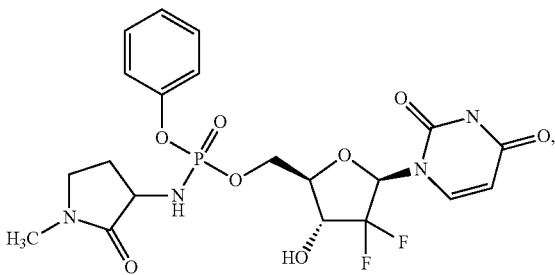
1.1(3)
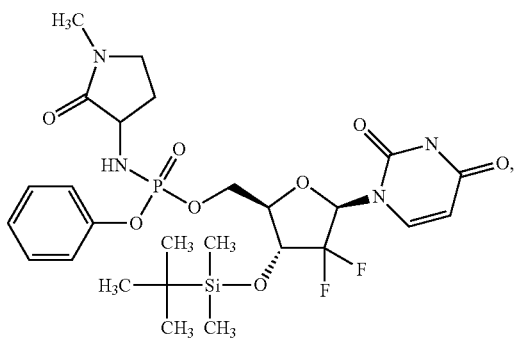
1.1(4)
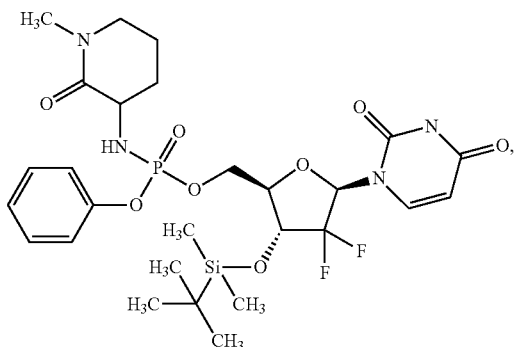
1.1(5)
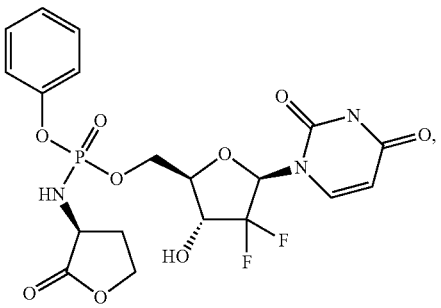
1.1(6)

1.2(1)
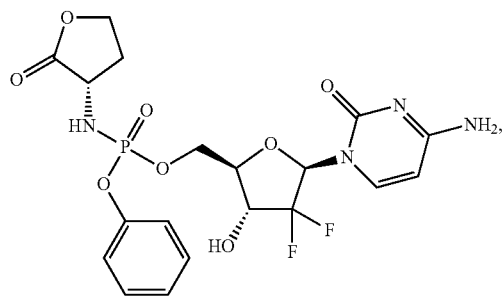
1.2(2)
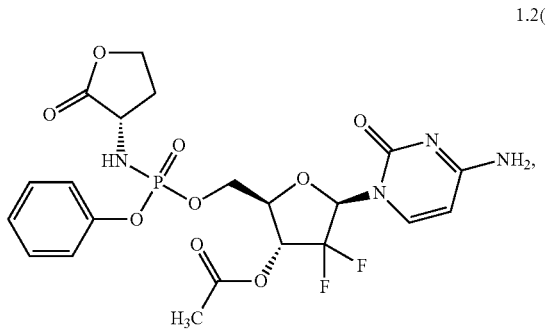
1.2(3)
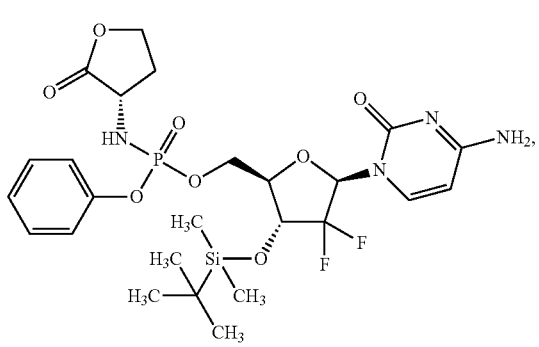
1.2(4)
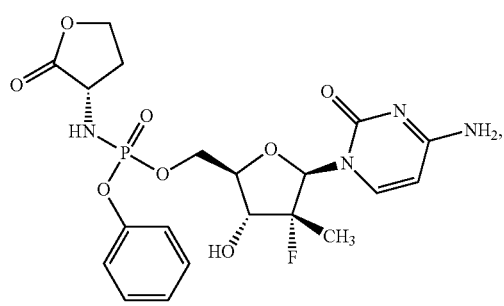
1.2(5)
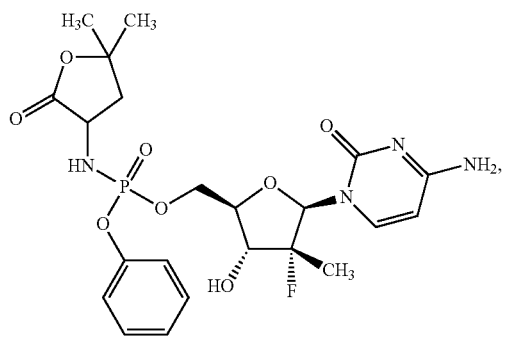
1.2(6)
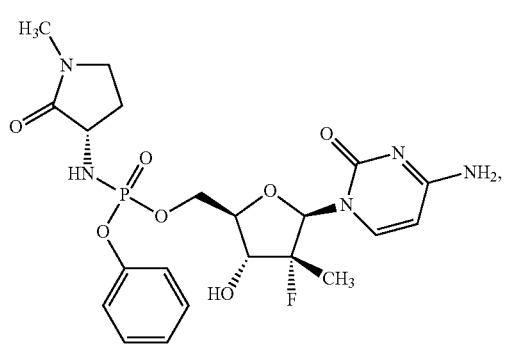
2.1(1)
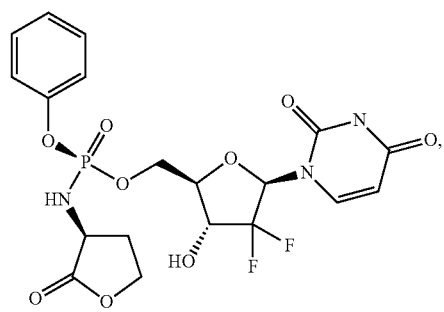
2.1(2)
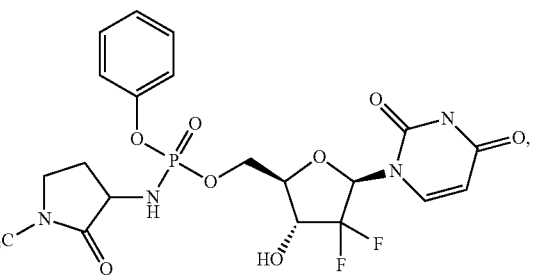
and -continued 2.2(1)

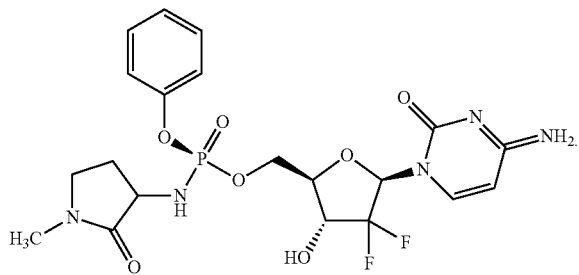

One embodiment of the invention provides a method for the preparation of a compound of formula 1, 1.1, or 1.2, or a stereoisomer thereof, interacting an amine of formula 3 with a compound of formula 4 and subsequently mixing with a compound of formula 6,

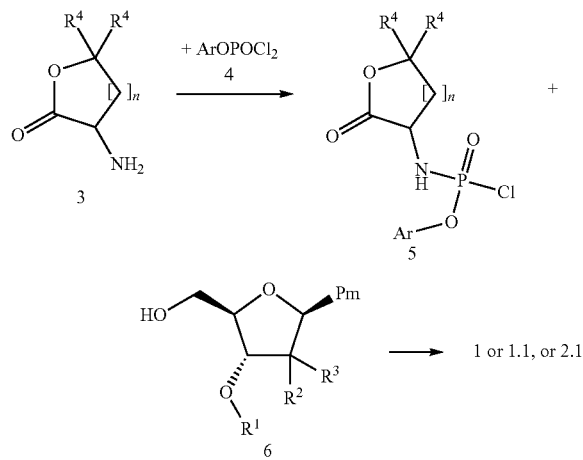

wherein Ar, n, $R^1$, $R^2$, $R^3$, $R^4$, and Pm are as defined herein above.

One of embodiment of the invention provides a method for the preparation of a compound of formula 1, 1.1, or 1.2, or a stereoisomer thereof, interacting a compound of formula 4 with a compound of formula 6 and subsequently mixing with an amine of formula 8,

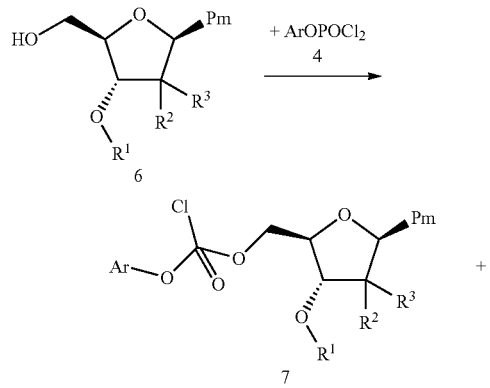

-continued

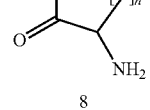

→ 1 or 1.1, or 2.1 wherein Ar, n, $R^1$, $R^2$, $R^3$, $R^4$, $R^9$, and Pm are as defined herein above.

Another embodiment of the invention is the method for the preparation of a compound of formula 1, 1.1, or 1.2, wherein $R^1$ is acyl, or a stereoisomer thereof, acidifying a compound of formula 1, wherein $R^1$ is hydrogen with acylating agent.

Another embodiment of the invention is the method for the preparation of a compound of formula 1, 1.1, or 1.2, wherein $R^1$ is tert-butyldimethylsilyl, or a stereoisomer thereof, mixing a tert-butyldimethylsilyl chloride with a compound of formula 1, wherein $R^1$ is hydrogen.

Resolution of racemic mixtures of compounds of general formula 1, 1.1, 1.2 into stereoisomers was carried out either by crystallization and/or LC, or performed by crystallization and/or HPLC.

The starting materials employed in the above synthesis of novel substituted phosphoramidic acid esters represented by the general formula 1 or 2, their stereoisomers, salts, hydrates, solvates, or crystalline forms, are commercially available compounds or they can be easily prepared by the methods known in the art. The quality of the compounds was monitored by LCMS and NMR.

The HCV replicon assay was used to determine the antiviral activity of substituted phosphoramidic acid esters of the general formula 1, 1.1, 1.2, 2, 2.1, and 2.2 (test compounds). The test cell line used in the HCV Replicon Assay was a human hepatoma cell line Huh7 incorporating the HCV replicon (genotype 1b, Con1 isolate). 96-well plates were seeded with cells at a density of $7.5 \times 10^3$ cells per well in 50 µl of assay media. Test compound stock solution was made up freshly in assay medium (DMEM 1×, Cellgro; cat. #10-013-CV) as a 2× stock. A total of 11 serial 3-fold dilutions of test compounds were prepared from the 2× stock in assay media ranging from 20 nM-0.2 pM final concentrations. At least 4 hours after cells were seeded, compound treatment was initiated by adding 50 µl of compound dilution to the plates. The final concentrations of compound therefore ranged from 10 nM-0.1 pM when diluted 1:1 the existing culture media. The final DMSO concentration was 0.5%. Cells and inhibitors incubated for 3 days at 37° C./5% $CO_2$. Media was removed from the plates via gentle tapping. Cells were fixed with 100 µl 1:1 acetone:methanol for 1 minute, washed three times with PBS buffer, and then blocked with 150 µl/well 10% Fetal Bovine Serum (FBS) in PBS for 1 hour at room temperature. Cells were washed three times with PBS buffer, and incubated with 100 µl/well anti-hepatitis C core mAb (Affinity BioReagents; cat. # MA1-080, 1 mg/ml stock diluted 1:4,000 in 10% FBS-PBS) for 2 hours at 37° C. Cells were washed three times with PBS and incubated with 100 µl/well HRP-Goat Anti-Mouse antibody (diluted 1:3.500 in 10% FBS-PBS) for 1 hour at 37° C. Cells were washed three times with PBS and developed with 100 µl/well OPD solution (1 OPD tablet+12 ml citrate/phosphate buffer+5 µl 30% $H_2O_2$ per plate) for 30 minutes in the dark at room temperature. The reaction was stopped with 100 µl/well of 2N $H_2SO_4$, and absorbance measured at $A_{490}$ X on a Victor[3] V 1420 multilabel counter (Perkin Elmer). The $EC_{50}$ values were calculated for test compounds from the resulting best-fit equations determined by Xlfit software.

The cytotoxicity of the test compounds were studied in parallel, using the same cell line, Huh7. Cell viability was determined using the ATPLite Kit (Perkin-Elmer, Boston, USA), according to manufacturer's instructions. 96-well black/transparent bottom plates were seeded with cells at a density of $7.5\times10^3$ cells per well in 50 μl medium. After 18 hours, compound treatment was initiated by adding 50 μl of compound dilution to the plates. Each compound dilution was tested in triplicates. Cells and inhibitors were then incubated for 96 hours at 37° C./5% $CO_2$. Plates were washed twice with PBS (0.2 ml/well), and then lysed by adding 0.05 ml/wel of lysis buffer (all reagent included with the ATPLite Kit). After rocking for 5 min on a rocking platform, 0.05 ml/well of the substrate buffer was added. After additional 5-min incubation, plates were kept in dark for 10 min, and the luminescence was read using TopCount NXT (Packard, Perkin Elmer). The $CC_{50}$ values for all test compounds were determined using XLfit 4.1 software.

The results of these studies show that the novel substituted phosphoramidic acid esters of the general formula 1, 1.1, 1.2, 2, 2.1, and 2.2 are potent HCV inhibitors in vitro with low cytotoxicity.

Inhibitory activity ($EC_{50}$) in HCV replicon assay conditions of some novel substituted phosphoramidic acid esters of the general formula 1, 1.1, 1.2, 2, 2.1, and 2.2 is shown in Table 1. Novel NS5B inhibitors of the general formula 1, 1.1, 1.2, 2, 2.1, and 2.2 exhibit a micromolar cytotoxicity and a nanomolar activity ($EC_{50}$), which is usually significantly higher than that of the known inhibitor PSI-7851 [$EC_{50}$=75 nM. E. Murakami, T. Tolstykh, H. Bao, C. Niu, H. M. Micolochick Steuer, D. Bao, W. Chang, C. Espiritu, S. Bansal, A. M. Lam, M. J. Otto, M. J. Sofia, P. A. Furman. Mechanism of Activation of PSI-7851 and Its Diastereoisomer PSI-7977. *J. Biol. Chem.*, 285(45), 34337-34347 (2010)].

Table 1. Activity of NS5B inhibitors of the general formula 1, 1.1, 1.2, 2, 2.1, and 2.2 against HCV genotype 1b (10% FBS)

TABLE 1

Activity of NS5B inhibitors of the general formula 1, 1.1, 1.2, 2, 2.1, and 2.2 against HCV genotype 1b (10% FBS)

| No. of inhibitor | Formula | $EC_{50}$, nM |
|---|---|---|
| 1(4) | [structure 1(4)] | 42.1 |
| 1(7) | [structure 1(7)] | 552.3 |

TABLE 1-continued

Activity of NS5B inhibitors of the general formula 1, 1.1, 1.2, 2, 2.1, and 2.2 against HCV genotype 1b (10% FBS)

| No. of inhibitor | Formula | $EC_{50}$, nM |
|---|---|---|
| 1(8) | 1(8) | 873.3 |
| 1(10) | 1(10) | 28.3 |
| 1(12) | 1(12) | 162.2 |
| 1.1.(1) | 1.1(1) | 458.9 |

TABLE 1-continued
Activity of NS5B inhibitors of the general formula 1, 1.1, 1.2, 2, 2.1, and 2.2 against HCV genotype 1b (10% FBS)
| No. of inhibitor | Formula | EC$_{50}$, nM |
|---|---|---|
| 1.1.(2) | 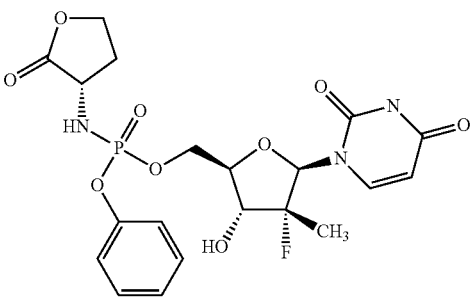<br>1.1(2) | 273.6 |
| 1.1.(4) | 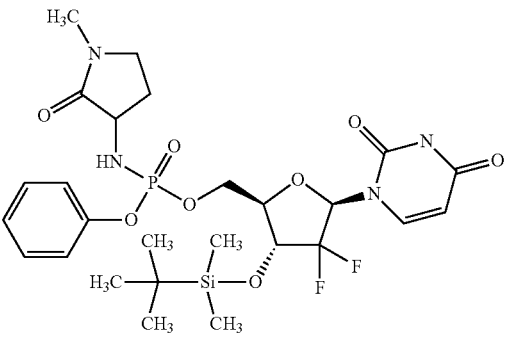<br>1.1(4) | 40.54 |
| 1.2.(1) | 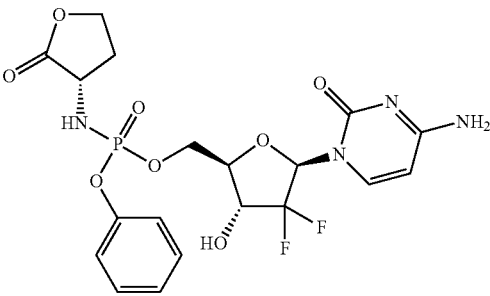 [SMILES: Nc1ccn([C@@H]2O[C@H](COP(=O)(N[C@H]3CCOC3=O)Oc3ccccc3)[C@@H](O)C2(F)F)c(=O)n1] | 19.8 |
| 1.2.(2) | 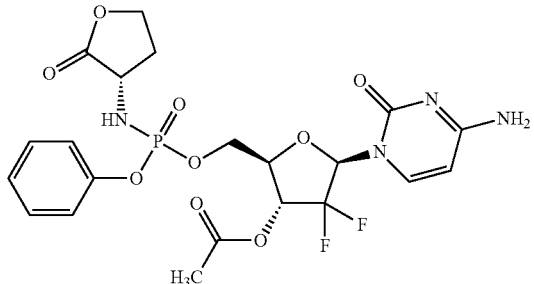<br>1.2(2) | 27.0 |

TABLE 1-continued

Activity of NS5B inhibitors of the general formula 1, 1.1, 1.2, 2, 2.1, and 2.2 against HCV genotype 1b (10% FBS)

| No. of inhibitor | Formula | EC$_{50}$, nM |
|---|---|---|
| 1.2.(3) | 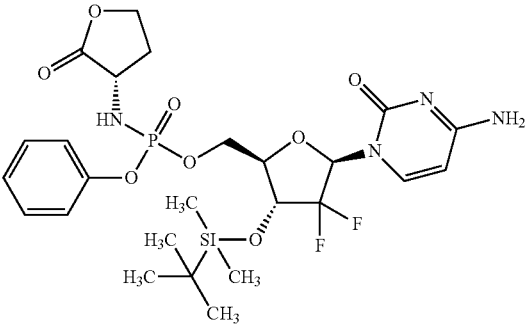<br>1.2(3) | 285.4 |
| 2.2.(1) | 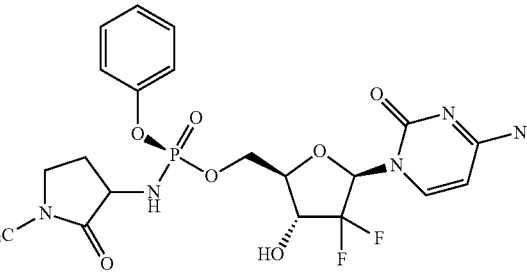<br>2.2(1) | 219.3 |
| PSI-7851 | 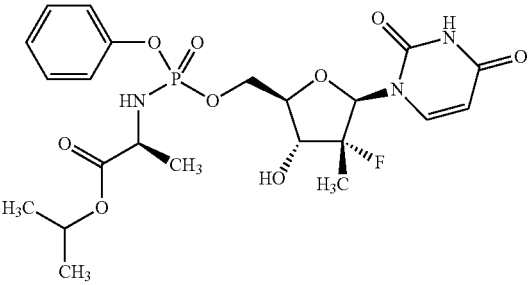 [SMILES: CC(C)OC(=O)[C@H](C)NP(=O)(OC[C@H]1O[C@@H](n2ccc(=O)[nH]c2=O)[C@](C)(F)[C@@H]1O)Oc1ccccc1] | 59.4* |

*the experimental data of the authors of the instant invention.

So, one embodiment of the present invention is a use of a substituted phosphoramidic acid ester of formula 1 or 2, or a pharmaceutically acceptable salt, a hydrate, a crystalline form or a stereoisomer thereof, as an active component for a medicine or a pharmaceutical composition in the manufacture of a medicament intended for the treating any condition which is the result of hepatitis C virus infection,

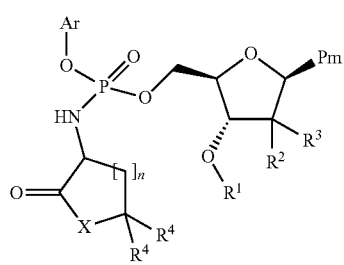

1

-continued

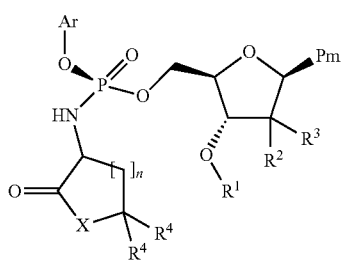

2 wherein:

R$^1$ is (i) hydrogen, (CH$_3$)$_2$[(CH$_3$)$_3$C]Si, a C$_2$-C$_6$acyl, optionally substituted with NR$^5$R$^6$ group, wherein R$^5$ and R$^6$ are independently hydrogen or a C$_1$-C$_4$ alkyl; (ii) 1-pyrrole-2-ylcarbonyl, piperidin-3-ylcarbonyl or piperidin-4-ylcarbonyl;

R$^2$ and R$^3$ are F; or R$^3$ is CH$_3$ and R$^2$ is F or OH;

R⁴ is hydrogen or methyl;

Ar is a phenyl, a pyridyl or a naphthyl, wherein phenyl, pyridyl or naphthyl are optionally substituted with at least one of $C_{1-3}$ alkyl, $C_{2-4}$ alkenyl, $C_{2-4}$ alkynyl, $C_{1-3}$ alkoxy, F, Cl, Br, I, nitro, cyano, —N$(C_{1-3}$ alkyl$)_2$;

Pm is 2,4-dioxo-3,4-dihydro-2H-pyrimidin-1-yl or 4-(4-amino-2-oxo-2H-pyrimidin-1-yl), in which amino group is optionally substituted with 1-pyrrole-2-ylcarbonyl, piperidin-3-ylcarbonyl, piperidin-4-ylcarbonyl or radical C(O)R⁸, wherein R⁸ is (i) a $C_1$-$C_4$alkyl, optionally substituted with NR⁶R⁷ group, wherein R⁶ and R⁷ are independently hydrogen or $C_1$-$C_4$ alkyl; (ii) a $C_{1-3}$ alkoxy optionally substituted with a phenyl;

X is O or N—R⁹, wherein R⁹ is a $C_1$-$C_4$alkyl, optionally substituted with OH or OCH₃;

n=1, 2 or 3.

According to the invention the best embodiment is a use of a compound, represented by the general formula 1, 2, 1.1, 1.2, 2.1, or 2.2, or a pharmaceutically acceptable salt, a hydrate, a crystalline form or a stereoisomer thereof, selected from the group consisting of:

((2R,3R,5R)-5-(4-amino-2-oxopyrimidin-1(2H)-yl)-4,4-difluoro-3-hydroxytetrahydrofuran-2-yl)methyl p-tolyl (S)-2-oxo-tetrahydrofuran-3-yl-phosphoramidate 1(1), ((2R,3R,5R)-5-(4-amino-2-oxopyrimidin-1(2H)-yl)-4,4-difluoro-3-hydroxytetrahydrofuran-2-yl)methyl 4-chlorophenyl (S)-2-oxo-tetrahydrofuran-3-yl-phosphoramidate 1(2), ((2R,3R,5R)-5-(4-amino-2-oxopyrimidin-1(2H)-yl)-4,4-difluoro-3-hydroxytetrahydrofuran-2-yl)methyl 2,4-dichlorophenyl (S)-2-oxo-tetrahydrofuran-3-yl-phosphoramidate 1(3), (2R,3R,5R)-5-(4-acetamido-2-oxopyrimidin-1(2H)-yl)-4,4-difluoro-2-(((S)—((S)-2-oxotetrahydrofuran-3-ylamino)(phenoxy)phosphoryloxy)methyl)tetrahydrofuran-3-yl acetate 1(4), benzyl 1-((2R,4R,5R)-4-(benzyloxycarbonyloxy)-3,3-difluoro-5-(((S)—((S)-(2-oxotetrahydrofuran-3-ylamino)(phenoxy)phosphoryloxy)methyl)tetrahydrofuran-2-yl)-2-oxo-1,2-dihydropyrimidin-4-ylcarbamate 1(5), benzyl 1-((2R,4R,5R)-4-(benzyloxycarbonyloxy)-3,3-difluoro-5-(((1-methyl-2-oxopyrrolidin-3-ylamino)(phenoxy)phosphoryloxy)methyl)tetrahydrofuran-2-yl)-2-oxo-1,2-dihydropyrimidin-4-ylcarbamate 1(6), benzyl 1-((2R,4R,5R)-4-(benzyloxycarbonyloxy)-3,3-difluoro-5-(((1-methyl-2-oxopiperidin-3-ylamino)(phenoxy)phosphoryloxy)methyl)tetrahydrofuran-2-yl)-2-oxo-1,2-dihydropyrimidin-4-ylcarbamate 1(7), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopiperidin-3-ylphosphoramidate 1(8), ((2R,3R,5R)-5-(4-amino-2-oxopyrimidin-1(2H)-yl)-4,4-difluoro-3-hydroxytetrahydrofuran-2-yl)methyl phenyl 2-oxooxepan-3-ylphosphoramidate 1(9), benzyl 1-((2R,4R,5R)-4-(benzyloxycarbonyloxy)-5-(((5,5-dimethyl-2-oxotetrahydrofuran-3-ylamino)(phenoxy)phosphoryloxy)methyl)-3,3-difluorotetrahydrofuran-2-yl)-2-oxo-1,2-dihydropyrimidin-4-ylcarbamate 1(10), ((2R,3R,5R)-5-(2,4-dioxo-3,4-dihydropyrimidin-1(2H)-yl)-4,4-difluoro-3-hydroxytetrahydrofuran-2-yl)methyl phenyl 5,5-dimethyl-2-oxotetrahydrofuran-3-yl-phosphoramidate 1(11), (R)-((2R,3R,5R)-5-(2,4-dioxo-3,4-dihydropyrimidin-1 (2H)-yl)-4,4-difluoro-3-hydroxytetrahydrofuran-2-yl) methyl phenyl methyl ((S)-2-oxotetrahydrofuran-3-yl) phosphoramidate 1(12), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-yl-phosphoramidate 1(13), ((2R,3R,5R)-5-(4-amino-2-oxopyrimidin-1(2H)-yl)-4,4-difluoro-3-hydroxytetrahydrofuran-2-yl)methyl phenyl 5,5-dimethyl-2-oxotetrahydrofuran-3-yl-phosphoramidate 1(14), (R)-((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 1(15), ((2R,3R,5R)-5-(2,4-dioxo-3,4-dihydropyrimidin-1(2H)-yl)-4,4-difluoro-3-hydroxytetrahydrofuran-2-yl)methyl phenyl 2-oxotetrahydrofuran-3-ylphosphoramidate 1.1(1), ((2R,3R,4R,5R)-5-(2,4-dioxo-3,4-dihydropyrimidin-1(2H)-yl)-4-fluoro-3-hydroxy-4-methyltetrahydrofuran-2-yl) methyl phenyl (S)-2-oxotetrahydrofuran-3-ylphosphoramidate 1.1(2), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 1.1(3), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopyrrolidin-3-ylphosphoramidate 1.1(4), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopiperidin-3-ylphosphoramidate 1.1(5), ((2R,3R,5R)-5-(2,4-dioxo-3,4-dihydropyrimidin-1(2H)-yl)-4,4-difluoro-3-hydroxy-tetrahydrofuran-2-yl)methyl phenyl (R)-2-oxo-tetrahydrofuran-3-ylphosphoramidate 1.1(6), (2R,3R,5R)-5-(4-amino-2-oxopyrimidin-1(2H)-yl)-4,4-difluoro-3-hydroxytetrahydrofuran-2-yl)methyl phenyl (S)-2-oxotetrahydrofuran-3-ylphosphoramidate 1.2(1), (2R,3R,5R)-5-(4-amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2), ((2R,3R,5R)-5-(4-amino-2-oxopyrimidin-1(2H)-yl)-3-(tert-butyldimethylsilyloxy)-4,4-difluorotetrahydrofuran-2-yl) methyl phenyl (S)-2-oxotetrahydrofuran-3-ylphosphoramidate 1.2(3), ((2R,3R,4R,5R)-5-(4-amino-2-oxopyrimidin-1(2H)-yl)-4-fluoro-3-hydroxy-4-methyltetrahydrofuran-2-yl)methyl phenyl (S)-2-oxotetrahydrofuran-3-ylphosphoramidate 1.2(4), ((2R,3R,4R,5R)-5-(4-amino-2-oxopyrimidin-1(2H)-yl)-4-fluoro-3-hydroxy-4-methyltetrahydrofuran-2-yl)methyl phenyl 5,5-dimethyl-2-oxotetrahydrofuran-3-ylphosphoramidate 1.2(5), ((2R,3R,4R,5R)-5-(4-amino-2-oxopyrimidin-1(2H)-yl)-4-fluoro-3-hydroxy-4-methyltetrahydrofuran-2-yl)methyl phenyl 1-methyl-2-oxopyrrolidin-3-ylphosphoramidate 1.2(6), (S)-((2R,3R,5R)-5-(2,4-dioxo-3,4-dihydropyrimidin-1(2H)-yl)-4,4-difluoro-3-hydroxytetrahydrofuran-2-yl)methyl phenyl ((R)-2-oxotetrahydrofuran-3-yl)phosphoramidate 2.1(1), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 2.1(2), and (S)-(2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 2.2(1).

One of embodiment of the present invention is a pharmaceutical composition for the treatment and/or prophylaxis of viral infections, including hepatitis C, comprising a pharmaceutically acceptable medium selected from fillers, carriers, diluents and equivalent average and a substituted phosphoramidic acid ester, represented by the formula 1 or 2, or a pharmaceutically acceptable salt, a hydrate, a crystalline form or a stereoisomer thereof,

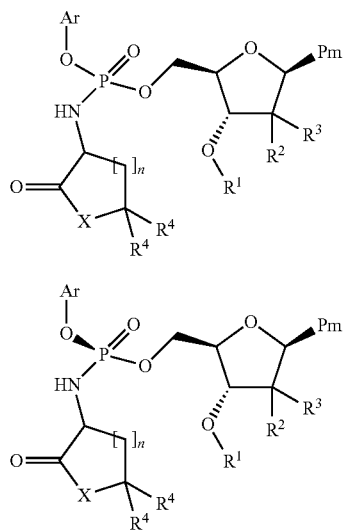

wherein:

$R^1$ is (i) hydrogen, a $(CH_3)_2[(CH_3)_3C]Si$, a $C_2$-$C_6$acyl, optionally substituted with $NR^5R^6$ group, wherein $R^5$ and $R^6$ are independently hydrogen or a $C_1$-$C_4$ alkyl; (ii) 1-pyrrole-2-ylcarbonyl, piperidin-3-ylcarbonyl or piperidin-4-ylcarbonyl;

$R^2$ and $R^3$ are F; or $R^3$ is $CH_3$ and $R^2$ is F or OH;

$R^4$ is hydrogen or methyl;

Ar is a phenyl, a pyridyl or a naphthyl, wherein phenyl, pyridyl or naphthyl are optionally substituted with at least one of $C_{1-3}$ alkyl, $C_{2-4}$ alkenyl, $C_{2-4}$ alkynyl, $C_{1-3}$ alkoxy, F, Cl, Br, I, nitro, cyano, —$N(C_{1-3}$ alkyl$)_2$;

Pm is 2,4-dioxo-3,4-dihydro-2H-pyrimidin-1-yl or 4-(4-amino-2-oxo-2H-pyrimidin-1-yl), in which amino group is optionally substituted with 1-pyrrole-2-ylcarbonyl, piperidin-3-ylcarbonyl, piperidin-4-ylcarbonyl or radical $C(O)R^8$, wherein $R^8$ is (i) a $C_1$-$C_4$alkyl, optionally substituted with $NR^6R^7$ group, wherein $R^6$ and $R^7$ are independently hydrogen or $C_1$-$C_4$ alkyl; (ii) a $C_{1-3}$ alkoxy optionally substituted with a phenyl;

X is O or N—$R^9$, wherein $R^9$ is a $C_1$-$C_4$alkyl, optionally substituted with OH or $OCH_3$;

n=1, 2 or 3.

According to the invention the best embodiment is a pharmaceutical composition, comprising a pharmaceutically acceptable medium selected from excipients, fillers, carriers, diluents and equivalent average and a substituted phosphoramidic acid ester represented by the general formula 1, 2, 1.1, 1.2, 2.1, or 2.2, or a pharmaceutically acceptable salt, a hydrate, a crystalline form or a stereoisomer thereof, selected from the group consisting of:

((2R,3R,5R)-5-(4-amino-2-oxopyrimidin-1(2H)-yl)-4,4-difluoro-3-hydroxytetrahydrofuran-2-yl)methyl p-tolyl (S)-2-oxo-tetrahydrofuran-3-yl-phosphoramidate 1(1), ((2R,3R,5R)-5-(4-amino-2-oxopyrimidin-1(2H)-yl)-4,4-difluoro-3-hydroxytetrahydrofuran-2-yl)methyl 4-chlorophenyl (S)-2-oxo-tetrahydrofuran-3-yl-phosphoramidate 1(2), ((2R,3R,5R)-5-(4-amino-2-oxopyrimidin-1(2H)-yl)-4,4-difluoro-3-hydroxytetrahydrofuran-2-yl)methyl 2,4-dichlorophenyl (S)-2-oxo-tetrahydrofuran-3-yl-phosphoramidate 1(3), (2R,3R,5R)-5-(4-acetamido-2-oxopyrimidin-1(2H)-yl)-4,4-difluoro-2-(((S)—((S)-2-oxotetrahydrofuran-3-ylamino)(phenoxy)phosphoryloxy)methyl)tetrahydrofuran-3-yl acetate 1(4), benzyl 1-((2R,4R,5R)-4-(benzyloxycarbonyloxy)-3,3-difluoro-5-(((S)—((S)-(2-oxotetrahydrofuran-3-ylamino)(phenoxy)phosphoryloxy)methyl)tetrahydrofuran-2-yl)-2-oxo-1,2-dihydropyrimidin-4-ylcarbamate 1(5), benzyl 1-((2R,4R,5R)-4-(benzyloxycarbonyloxy)-3,3-difluoro-5-(((1-methyl-2-oxopyrrolidin-3-ylamino)(phenoxy)phosphoryloxy)methyl)tetrahydrofuran-2-yl)-2-oxo-1,2-dihydropyrimidin-4-ylcarbamate 1(6), benzyl 1-((2R,4R,5R)-4-(benzyloxycarbonyloxy)-3,3-difluoro-5-(((1-methyl-2-oxopiperidin-3-ylamino)(phenoxy)phosphoryloxy)methyl)tetrahydrofuran-2-yl)-2-oxo-1,2-dihydropyrimidin-4-ylcarbamate 1(7), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopiperidin-3-ylphosphoramidate 1(8), ((2R,3R,5R)-5-(4-amino-2-oxopyrimidin-1(2H)-yl)-4,4-difluoro-3-hydroxytetrahydrofuran-2-yl)methyl phenyl 2-oxooxepan-3-ylphosphoramidate 1(9), benzyl 1-((2R,4R,5R)-4-(benzyloxycarbonyloxy)-5-(((5,5-dimethyl-2-oxotetrahydrofuran-3-ylamino)(phenoxy)phosphoryloxy)methyl)-3,3-difluorotetrahydrofuran-2-yl)-2-oxo-1,2-dihydropyrimidin-4-ylcarbamate 1(10), ((2R,3R,5R)-5-(2,4-dioxo-3,4-dihydropyrimidin-1(2H)-yl)-4,4-difluoro-3-hydroxytetrahydrofuran-2-yl)methyl phenyl 5,5-dimethyl-2-oxotetrahydrofuran-3-ylphosphoramidate 1(11), (R)-((2R,3R,5R)-5-(2,4-dioxo-3,4-dihydropyrimidin-1(2H)-yl)-4,4-difluoro-3-hydroxytetrahydrofuran-2-yl)methyl phenyl methyl ((S)-2-oxotetrahydrofuran-3-yl)phosphoramidate 1(12), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-yl-phosphoramidate 1(13), ((2R,3R,5R)-5-(4-amino-2-oxopyrimidin-1(2H)-yl)-4,4-difluoro-3-hydroxytetrahydrofuran-2-yl)methyl phenyl 5,5-dimethyl-2-oxotetrahydrofuran-3-yl-phosphoramidate 1(14), (R)-((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 1(15), ((2R,3R,5R)-5-(2,4-dioxo-3,4-dihydropyrimidin-1(2H)-yl)-4,4-difluoro-3-hydroxytetrahydrofuran-2-yl)methyl phenyl 2-oxotetrahydrofuran-3-ylphosphoramidate 1.1(1), ((2R,3R,4R,5R)-5-(2,4-dioxo-3,4-dihydropyrimidin-1(2H)-yl)-4-fluoro-3-hydroxy-4-methyltetrahydrofuran-2-yl)methyl phenyl (S)-2-oxotetrahydrofuran-3-ylphosphoramidate 1.1(2), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 1.1(3), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopyrrolidin-3-ylphosphoramidate 1.1(4), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopiperidin-3-ylphosphoramidate 1.1(5), ((2R,3R,5R)-5-(2,4-dioxo-3,4-dihydropyrimidin-1(2H)-yl)-4,4-difluoro-3-hydroxy-tetrahydrofuran-2-yl)methyl phenyl (R)-2-oxo-tetrahydrofuran-3-ylphosphoramidate 1.1(6), (2R,3R,5R)-5-(4-amino-2-oxopyrimidin-1(2H)-yl)-4,4-difluoro-3-hydroxytetrahydrofuran-2-yl)methyl phenyl (S)-2-oxotetrahydrofuran-3-ylphosphoramidate 1.2(1), (2R,3R,5R)-5-(4-amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2), ((2R,3R,5R)-5-(4-amino-2-oxopyrimidin-1(2H)-yl)-3-(tert-butyldimethylsilyloxy)-4,4-difluorotetrahydrofuran-2-yl)methyl phenyl (S)-2-oxotetrahydrofuran-3-ylphosphoramidate 1.2(3), ((2R,3R,4R,5R)-5-(4-amino-2-oxopyrimidin-1(2H)-yl)-4-fluoro-3-hydroxy-4-methyltetrahydro furan-2-yl)methyl phenyl (S)-2-oxotetrahydrofuran-3-ylphosphoramidate 1.2(4), ((2R,3R,4R,5R)-5-(4-amino-2-oxopyrimidin-1(2H)-yl)-4-fluoro-3-hydroxy-4-methyltetrahydro furan-2-yl)methyl phenyl 5,5-dimethyl-2-oxotetrahydrofuran-3-ylphosphoramidate 1.2(5), ((2R,3R,4R,5R)-5-(4-amino-2-oxopyrimidin-1(2H)-yl)-4-fluoro-3-hydroxy-4-methyltetrahydro furan-2-yl)methyl phenyl 1-methyl-2-oxopyrrolidin-3-ylphosphoramidate 1.2(6), (S)-((2R,3R,5R)-5-(2,4-dioxo-3,4-dihydropyrimidin-1(2H)-yl)-4,4-difluoro-3-hydroxytetrahydrofuran-2-yl)methyl phenyl ((R)-2-oxotetrahydrofuran-3-yl)phosphoramidate 2.1(1), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 2.1(2), and (S)-(2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 2.2(1).

The best pharmaceutical composition may further comprise at least one of a drug substance selected from the group consisting of: an inosine 5 monophosphate dehydrogenase inhibitor, HCV protease NS3 inhibitor, HCV protease NS3/4A inhibitor, and RNA polymerase NS5A inhibitor.

The best pharmaceutical composition is in the form of a tablet, a capsule, an injection, a liniment, a rectal gel, or a rectal suspension placed in a pharmaceutically acceptable packing.

One of embodiment provides a method for inhibiting HCV RNA polymerase NS5B comprising contacting HCV RNA polymerase NS5B with a compound of formula 1 or 2, or a pharmaceutically acceptable salt, a hydrate, a crystalline form or a stereoisomer thereof One of embodiment of the present invention provides a method for treating a disease caused by hepatitis C virus comprising administering compound of formula 1 or 2, or a pharmaceutically acceptable salt, a hydrate, a crystalline form or a stereoisomer thereof, in an effective dosage to a subject in need thereof,

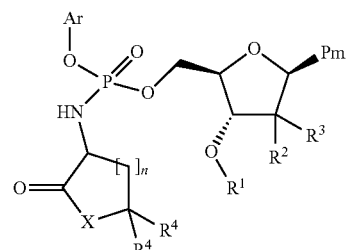

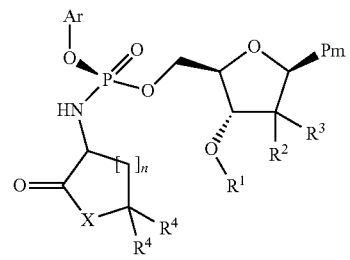

wherein:

$R^1$ is (i) hydrogen, a $(CH_3)_2[(CH_3)_3C]Si$, a $C_2$-$C_6$acyl, optionally substituted with $NR^5R^6$ group, wherein $R^5$ and $R^6$ are independently hydrogen or a $C_1$-$C_4$ alkyl; (ii) 1-pyrrole-2-ylcarbonyl, piperidin-3-ylcarbonyl or piperidin-4-ylcarbonyl;

$R^2$ and $R^3$ are F; or $R^3$ is $CH_3$ and $R^2$ is F or OH;

$R^4$ is hydrogen or methyl;

Ar is a phenyl, a pyridyl or a naphthyl, wherein phenyl, pyridyl or naphthyl are optionally substituted with at least one of $C_{1-3}$ alkyl, $C_{2-4}$ alkenyl, $C_{2-4}$ alkynyl, $C_{1-3}$ alkoxy, F, Cl, Br, I, nitro, cyano, —$N(C_{1-3}$ alkyl$)_2$;

Pm is 2,4-dioxo-3,4-dihydro-2H-pyrimidin-1-yl or 4-(4-amino-2-oxo-2H-pyrimidin-1-yl), in which amino group is optionally substituted with 1-pyrrole-2-ylcarbonyl, piperidin-3-ylcarbonyl, piperidin-4-ylcarbonyl or radical $C(O)R^8$, wherein $R^8$ is (i) a $C_1$-$C_4$alkyl, optionally substituted with $NR^6R^7$ group, wherein $R^6$ and $R^7$ are independently hydrogen or $C_1$-$C_4$ alkyl; (ii) a $C_{1-3}$ alkoxy optionally substituted with a phenyl;

X is O or N—$R^9$, wherein $R^9$ is a $C_1$-$C_4$alkyl, optionally substituted with OH or $OCH_3$;

n=1, 2 or 3.

According to the invention the best embodiment is a method for treating a disease caused by hepatitis C virus comprising administering a substituted phosphoramidic acid ester represented by the general formula 1, 2, 1.1, 1.2, 2.1, or 2.2, or a pharmaceutically acceptable salt, a hydrate, a crystalline form or a stereoisomer thereof, in an effective dosage to a subject in need thereof, selected from the group consisting of:

((2R,3R,5R)-5-(4-amino-2-oxopyrimidin-1(2H)-yl)-4,4-difluoro-3-hydroxytetrahydrofuran-2-yl)methyl p-tolyl (S)-2-oxo-tetrahydrofuran-3-yl-phosphoramidate 1(1), ((2R,3R,5R)-5-(4-amino-2-oxopyrimidin-1(2H)-yl)-4,4-difluoro-3-hydroxytetrahydrofuran-2-yl)methyl 4-chlorophenyl (S)-2-oxo-tetrahydrofuran-3-yl-phosphoramidate 1(2), ((2R,3R,5R)-5-(4-amino-2-oxopyrimidin-1(2H)-yl)-4,4-difluoro-3-hydroxytetrahydrofuran-2-yl)methyl 2,4-dichlorophenyl (S)-2-oxo-tetrahydrofuran-3-yl-phosphoramidate 1(3), (2R,3R,5R)-5-(4-acetamido-2-oxopyrimidin-1(2H)-yl)-4,4-difluoro-2-(((S)—((S)-2-oxotetrahydrofuran-3-ylamino)(phenoxy)phosphoryloxy)methyl)tetrahydrofuran-3-yl acetate 1(4), benzyl 1-((2R,4R,5R)-4-(benzyloxycarbonyloxy)-3,3-difluoro-5-(((S)—((S)-(2-oxotetrahydrofuran-3-ylamino)(phenoxy)phosphoryloxy)methyl)tetrahydrofuran-2-yl)-2-oxo-1,2-dihydropyrimidin-4-ylcarbamate 1(5), benzyl 1-((2R,4R,5R)-4-(benzyloxycarbonyloxy)-3,3-difluoro-5-(((1-methyl-2-oxopyrrolidin-3-ylamino)(phenoxy)phosphoryloxy)methyl)tetrahydrofuran-2-yl)-2-oxo-1,2-dihydropyrimidin-4-ylcarbamate 1(6), benzyl 1-((2R,4R,5R)-4-(benzyloxycarbonyloxy)-3,3-difluoro-5-(((1-methyl-2-oxopiperidin-3-ylamino)(phenoxy)phosphoryloxy)methyl)tetrahydrofuran-2-yl)-2-oxo-1,2-dihydropyrimidin-4-ylcarbamate 1(7), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopiperidin-3-ylphosphoramidate 1(8), ((2R,3R,5R)-5-(4-amino-2-oxopyrimidin-1(2H)-yl)-4,4-difluoro-3-hydroxytetrahydrofuran-2-yl)methyl phenyl 2-oxooxepan-3-ylphosphoramidate 1(9), benzyl 1-((2R,4R,5R)-4-(benzyloxycarbonyloxy)-5-(((5,5-dimethyl-2-oxotetrahydrofuran-3-ylamino)(phenoxy)phosphoryloxy)methyl)-3,3-difluorotetrahydrofuran-2-yl)-2-oxo-1,2-dihydropyrimidin-4-ylcarbamate 1(10), ((2R,3R,5R)-5-(2,4-dioxo-3,4-dihydropyrimidin-1(2H)-yl)-4,4-difluoro-3-hydroxytetrahydrofuran-2-yl)methyl phenyl 5,5-dimethyl-2-oxotetrahydrofuran-3-ylphosphoramidate 1(11), (R)-((2R,3R,5R)-5-(2,4-dioxo-3,4-dihydropyrimidin-1(2H)-yl)-4,4-difluoro-3-hydroxytetrahydrofuran-2-yl)methyl phenyl methyl ((S)-2-oxotetrahydrofuran-3-yl)phosphoramidate 1(12), ((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-yl-phosphoramidate 1(13), ((2R,3R,5R)-5-(4-amino-2-oxopyrimidin-1(2H)-yl)-4,4-difluoro-3-hydroxytetrahydrofuran-2-yl)methyl phenyl 5,5-dimethyl-2-oxotetrahydrofuran-3-yl-phosphoramidate 1(14), (R)-((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 1(15), ((2R,3R,5R)-5-(2,4-dioxo-3,4-dihydropyrimidin-1(2H)-yl)-4,4-difluoro-3-hydroxytetrahydrofuran-2-yl)methyl phenyl 2-oxotetrahydrofuran-3-ylphosphoramidate 1.1(1), ((2R,3R,4R,5R)-5-(2,4-dioxo-3,4-dihydropyrimidin-1(2H)-yl)-4-fluoro-3-hydroxy-4-methyltetrahydrofuran-2-yl)methyl phenyl (S)-2-oxotetrahydrofuran-3-ylphosphoramidate 1.1(2), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 1.1(3), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopyrrolidin-3-ylphosphoramidate 1.1(4), ((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopiperidin-3-ylphosphoramidate 1.1(5), ((2R,3R,5R)-5-(2,4-dioxo-3,4-dihydropyrimidin-1(2H)-yl)-4,4-difluoro-3-hydroxytetrahydrofuran-2-yl)methyl phenyl (R)-2-oxo-tetrahydrofuran-3-ylphosphoramidate 1.1(6), (2R,3R,5R)-5-(4-amino-2-oxopyrimidin-1(2H)-yl)-4,4-difluoro-3-hydroxytetrahydrofuran-2-yl)methyl phenyl (S)-2-oxotetrahydrofuran-3-ylphosphoramidate 1.2(1), (2R,3R,5R)-5-(4-amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2), ((2R,3R,5R)-5-(4-amino-2-oxopyrimidin-1(2H)-yl)-3-(tert-butyldimethylsilyloxy)-4,4-difluorotetrahydrofuran-2-yl)methyl phenyl (S)-2-oxotetrahydrofuran-3-ylphosphoramidate 1.2(3), ((2R,3R,4R,5R)-5-(4-amino-2-oxopyrimidin-1(2H)-yl)-4-fluoro-3-hydroxy-4-methyltetrahydrofuran-2-yl)methyl phenyl (S)-2-oxotetrahydrofuran-3-ylphosphoramidate 1.2(4), ((2R,3R,4R,5R)-5-(4-amino-2-oxopyrimidin-1(2H)-yl)-4-fluoro-3-hydroxy-4-methyltetrahydrofuran-2-yl)methyl phenyl 5,5-dimethyl-2-oxotetrahydrofuran-3-ylphosphoramidate 1.2(5), ((2R,3R,4R,5R)-5-(4-amino-2-oxopyrimidin-1(2H)-yl)-4-fluoro-3-hydroxy-4-methyltetrahydrofuran-2-yl)methyl phenyl 1-methyl-2-oxopyrrolidin-3-ylphosphoramidate 1.2(6), (S)-((2R,3R,5R)-5-(2,4-dioxo-3,4-dihydropyrimidin-1(2H)-yl)-4,4-difluoro-3-hydroxytetrahydro furan-2-yl)methyl phenyl ((R)-2-oxotetrahydrofuran-3-yl)phosphoramidate 2.1(1), ((2R,3R,5R)-5-(2,4-dioxo-3,4-dihydropyrimidin-1(2H)-yl)-4,4-difluoro-3-hydroxytetrahydrofuran-2-yl)methyl phenyl 1-methyl-2-oxopyrrolidin-3-ylphosphoramidate 2.1(2), and (S)-(2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-ylphosphoramidate 2.2(1).

Clinical dosage of a pharmaceutical composition comprising as an active ingredient at least one substituted phosphoramidic acid ester of the general formula 1, 2, 1.1, 1.2, 2.1, or 2.2, or a pharmaceutically acceptable salt, a hydrate, a crystalline form or a stereoisomer thereof, may be corrected depending on: therapeutic efficiency and bio-accessibility of active ingredients in patients' organism, rate of their exchange and removal from organism, and age, gender, and severity of patient's symptoms. Thus, the daily intake for adults normally being 10~500 mg. Accordingly, the above effective dosages are to be taken into consideration while preparing pharmaceutical composition according to the present invention, each dose unit should contain 10~500 mg of a substituted phosphoramidic acid ester of the general formula 1, 2, 1.1, 1.2, 2.1, or 2.2, or a pharmaceutically acceptable salt, a hydrate, a crystalline form or a stereoisomer thereof.

Following the instructions of physician or pharmacist, the medicaments may be taken several times over specified periods of time (preferably, from one to six times).

One of embodiment of the invention is directed to a therapeutic cocktail intended for prophylaxis and treatment of human and animals infected with flaviviruses including hepatitis C virus, comprising as one of the ingredients therapeutically effective amount of a substituted phosphoramidic acid ester of the general formula 1, 2, 1.1, 1.2, 2.1, or 2.2, or a pharmaceutically acceptable salt, a hydrate, a crystalline form or a stereoisomer thereof, or pharmaceutical composition comprising a substituted phosphoramidic acid ester of the general formula 1, 2, 1.1, 1.2, 2.1, or 2.2, or a pharmaceutically acceptable salt, a hydrate, a crystalline form or a stereoisomer thereof.

Therapeutic cocktail intended for prophylaxis and treatment of mentioned above flavivirus diseases including hepatitis C together with the medicaments disclosed in the invention may include other active ingredients, such as: inhibitors of inosine-5-monophosphate dehydrogenase,
for example, Ribavirin (allowed) and Ribamidine; inhibitors of NS3 hepatisis C protease, for example, Telaprevir and boceprevir; inhibitors of RNK-polimerazy NS5A, for example, VX222, R7128, PF-868554, ANA598; alpha-glucosidase inhibitors, for example, aminocarbohydrate Selgozivir; and also TLR-receptor agonists, hepatoprotectors, cyclosporines, various proteins (for example, interferons), antibodies, vaccines etc.

For combination therapies any classes of agents that may be useful when combined with compounds of the present invention include, for example, nucleoside and non-nucleoside inhibitors of the HCV polymerase, protease inhibitoprs, helicase inhibitors, NS4A inhibitors and medicinal agents that functionally inhibit the internal ribosomal entry site (IRES) and other medicaments that inhibit cell attachment or virus entry, HCV RNA translation, replication or HCV maturation or virus release.

Specific compounds in these classes and useful in this invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor) VX-500, VX-813, PHX-1766, PHX2054, IDX-136, IDX-316, ABT-450 EP-013420 (and congeners) and the Nucleosidic HCV polymerase (replicase) inhibitors useful in the invention include, but are not limited to, R7128, PSI-7851, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleoside and nucleotide; and 7'-deaza modified nucleoside and nucleotide. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (for example, without limitation, DEBIO compounds, NM-811, as well as cyclosporine and its derivatives), kinase inhibitors, inhibitors of heat shock proteins (for example, HSP90, HSP70), other immunomodulatory agents that may include, without limitation, interferons (alpha-, beta-, omega-, gamma-, lambda or synthetic), such as Intron A™, Roferon-A™, Canferon-A300™, Advaferon™, Infergen™, Humoferon™, Sumiferon MP™, Alfaferon™, IFN-β™, Feron™, and the like, polyethylene glycol derivatized (pegylated) interferon compounds, such as: PEG interferon-α-2a (Pegasys™), PEG interferon-α-2b (PEGIntron™), pegylated IFN-α-con 1 and the like; long acting formulations and derivatives of interferon compounds, such as albumin-fused interferon, Albuferon™, Locteron™, and the like; interferons with various types of controlled delivery systems (e.g. ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists, such as: CpG-10101 (action), isotorabine, ANA773 and the like; thymosin α-1, ANA-245 and ANA-246, histamine dihydrochloride, propagermanium; tetrachlorodecaoxide; ampligen; IMP-321; KRN-7000; antibodies, such as: civacir, XTL-6865 and the like and prophylactic and therapeutic vaccines, such as: Inno Vac, HCV E1E2/MF59 and the like. In addition, any of the above-described methods involving adminestering an NS5A inhibitor, a Type 1 interferon receptor agonist (e.g., an IFN-α) and a Type II interferon receptor agonist (e.g., IFN-γ) can be augmented by administration of an effective amount of TNF-α antagonist. Exemplary, non-limiting TNF-α antagonists that are suitable for use in such combination therapies include ENBREL™ and HUMIRA™.

In addition, NS5A inhibitors of the present invention may be used in combination with antiprotozoans and other antivirals thought to be effective in the treatment of HCV infection, such as, the prodrug nitazoxanide. Nitazoxanide can be used as an agent in combination with the compounds disclosed in this invention as well as in combination with other agents useful in treating HCV infection such as peginterferon alfa-2a and ribavarin (see, for example, Rossignol, J F and Keeffe, E B, *Future Microbiol.* 3:539-545, 2008).

NS5A inhibitors of the present invention may also be used in combination with alternative forms of interferons and pegylated interferons, ribavirin or its analogs (e.g., Tarabavarin, levovirion), microRNA, small interfering RNA compounds (e.g., SIRPLEX-140-N) and the like, nucleotide or nucleoside analogs, immonoglobulins, hepatoprotectants, anti-inflammatory agents and other inhibitiors of NS5A. Inhibitors of other targets in the HCV life cycle include NS3 helicase inhibitors; NS4A co-factor inhibitors, antisense oligonucleotide inhibitors, such as ISIS-14803, AVI-4065 and the like; vector-encoded short hairpin RNA (shRNA); HCV specific ribozymes such as heptazyme, RPI, 139199 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative compounds HCV inhibitor compounds include those disclosed in the known scientific and patent publications.

Additionally, combinations of, for example, ribavirin and interferon may be administered as multiple combination therapy with, at least one substituted phosphoramidic acid esters of the general formula 1, 2, 1.1, 1.2, 2.1, or 2.2, or a pharmaceutically acceptable salt, a hydrate, a crystalline form or a stereoisomer thereof. The present invention is not limited to the aforementioned classes or compounds and contemplates known and new compounds and combinations of biologically active agents. It is intended that combination therapies of the present invention include any chemically compatible combination of compounds of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the present invention or where one treatment comprises a compound of the present invention and the other comprises one or more biologically active agents) or it can be treatment with both agents at the same time. Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. For any particular subject specific dosage regimens and schedules may be adjusted over time according to the individual's need and the professional judgement of the person administering or superivising the administration of the combination therapy.

Although the foregoing invention has been described in some detail by way of illustration and example for purposes of clarity of understanding, it will be readily apparent to one of ordinary skill in the art in light of the teaching of this invention that certain changes and modifications may be made thereto without departing from the spirit or scope of the invention as defined in the claims.

Below the invention is described by means of specific examples, which illustrate but not limit the scope of the invention

EXAMPLE 1

General protocol for the preparation of compounds of general formula 1, 1.1 and 1.2. To a solution of 0.8 mmol of aryl phosphorodichloridate 4 in 5 mL of MeCN was added dropwise a solution of 0.67 mmol of alcohol 6 and N-methylimidazole (55 mg, 0.67 mmol) in 4 mL of MeCN at −10° C. and mixture was stirred at −10° C. for 5 h. Then a solution of 0.8 mmol of amine hydrochloride 8 and N-methylimidazole (131 mg, 1.6 mmol) in 10 mL of DCM was added and mixture was stirred at ambient temperature for 12 h. The mixture was concentrated in vacuo. Purification of the product was carried out by HPLC method without acid in the mobile phase. Compounds of general formula 1, 1.1 and 1.2 were obtained, among them:
benzyl 1-((2R,4R,5R)-4-(benzyloxycarbonyloxy)-3,3-difluoro-5-(((1-methyl-2-oxopyrrolidin-3-ylamino)(phenoxy)phosphoryloxy)methyl)-tetrahydrofuran-2-yl)-2-oxo-1,2-dihydropyrimidin-4-ylcarbamate 1(6), LC-MS (ESI) [M+H]+ 784;
benzyl 1-((2R,4R,5R)-4-(benzyloxycarbonyloxy)-3,3-difluoro-5-(((1-methyl-2-oxopiperidin-3-ylamino)(phenoxy)phosphoryloxy)methyl)-tetrahydrofuran-2-yl)-2-oxo-1,2-dihydropyrimidin-4-ylcarbamate 1(7), LC-MS (ESI) [M+H]+ 798;
((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopiperidin-3-ylphosphoramidate 1.1(5) LC-MS (ESI) [M+H]+ 645.

EXAMPLE 2

(2R,3R,5R)-5-(4-acetamido-2-oxopyrimidin-1(2H)-yl)-4,4-difluoro-2-(((S)—((S)-2-oxotetrahydrofuran-3-ylamino)phenoxy)phosphoryloxy)methyl)tetrahydrofuran-3-yl acetate 1(4) and (2R,3R,5R)-5-(4-amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2). To a solution of compound 1.2(1) (100 mg, 0.2 mmol) in 2 mL of pyridine was added Ac$_2$O (41 mg, 0.4 mmol) and mixture was stirred for 12 h. The solution was evaporated in vacuo, the residue dissolved in DCM, washed with water, dried over Na$_2$SO$_4$, evaporated in vacuo and separated by HPLC without acid. Compound 1.2(2) was obtained, LC-MS (ESI) [M+H]+ 545, $^1$H NMR (DMSO-d$_6$, 400 MHz) δ 7.44 (m, 5H), 7.23 (m, 3H), 6.18 (m, 2H), 5.74, 5.79 (2 d, J=7.4 Hz, 1H), 5.38 (brm, 1H), 4.40 (m, 3H), 4.26 (m, 2H), 4.15 (m, 2H), 2.35 (m, 1H), 2.14, 2.15 (2 s, 3H), 2.01 (m, 1H) and compound 1(4), LC-MS (ESI) [M+H]+ 587, $^1$H NMR (DMSO-d$_6$, 400 MHz) δ 11.05 (s, 1H), 7.93, 8.04 (2 d, J=7.6 Hz, 1H), 7.38 (m, 2H), 7.23 (m, 5H), 6.34 (m, 1H), 6.17 (m, 1H), 5.42 (m, 1H), 4.45 (m, 3H), 4.27 (m, 2H), 4.16 (m, 2H), 2.35 (m, 1H), 2.15, 2.16 (2 s, 3H), 2.12 (s, 3H), 2.01 (m, 1H).

EXAMPLE 3

((2R,3R,5R)-5-(4-Amino-2-oxopyrimidin-1(2H)-yl)-3-(tert-butyldimethyl-silyloxy)-4,4-difluoro-tetrahydrofuran-2-yl)methyl phenyl (S)-2-oxo-tetrahydrofuran-3-ylphosphoramidate 1.2(3). To a solution of compound 1.2(1) (112 mg, 0.22 mmol) in 1 mL of pyridine was added TBDMSCl (84 mg, 56 mmol) and mixture was stirred at 50° C. for 48 h. The solution was evaporated in vacuo, the residue dissolved in DCM, washed with water, dried over Na$_2$SO$_4$, evaporated in vacuo and purified by chromatography on SiO$_2$ (eluent MeCN: i-PrOH=10:1). This gave compound 1.2(3), LC-MS (ESI) [M+H]+ 617, $^1$H NMR (DMSO-d$_6$, 400 MHz) δ 7.50 (m, 1H), 7.40 (m, 4H), 7.22 (m, 3H), 6.20 (m, 1H), 6.12 (m, 1H), 5.78 (m, 1H), 4.38 (m, 2H), 4.26 (m, 3H), 4.12 (m, 2H), 2.33 (m, 1H), 0.88 (s, 9H), 0.10 (s, 3H), 0.09 (s, 3H).

EXAMPLE 4

Benzyl 1-((2R,4R,5R)-4-(benzyloxycarbonyloxy)-5-(((5,5-dimethyl-2-oxotetrahydrofuran-3-ylamino)(phenoxy)phosphoryloxy)methyl)-3,3-difluorotetrahydrofuran-2-yl)-2-oxo-1,2-dihydropyrimidin-4-ylcarbamate 1(10), and ((2R,3R,5R)-5-(4-amino-2-oxopyrimidin-1(2H)-yl)-4,4-difluoro-3-hydroxytetrahydrofuran-2-yl)methyl phenyl 5,5-dimethyl-2-oxotetrahydrofuran-3-yl-phosphoramidate 1(14), were prepared according to the following scheme:

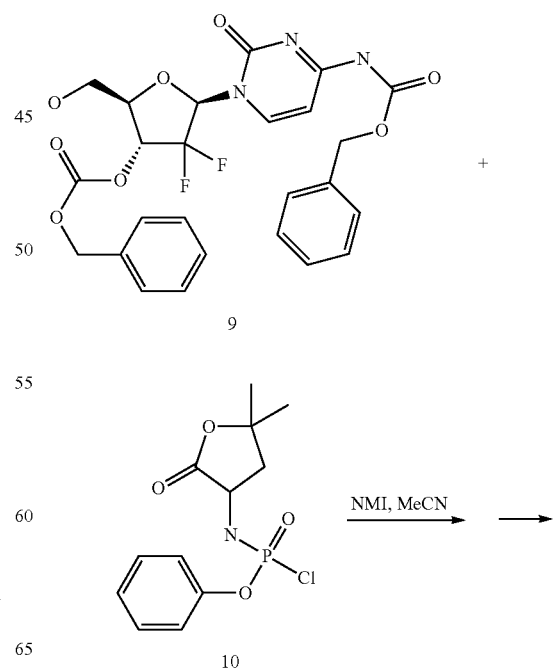

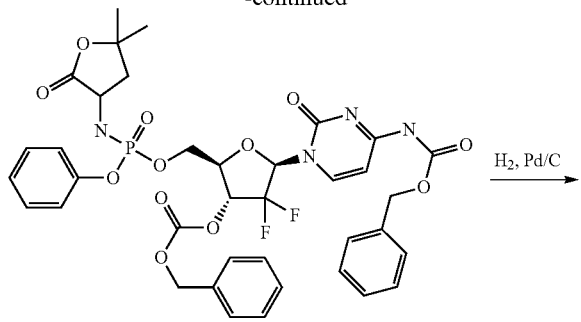

1.10

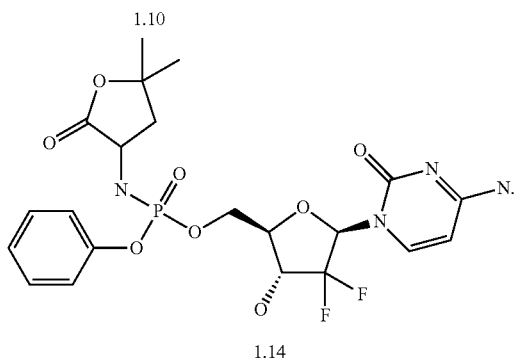

1.14

A solution of 673 mg (1.27 mmol) of bis-Cbz-gemcitabine 9, 500 mg (1.65 mmol) of phenyl 5,5-dimethyl-2-oxo-tetrahydrofuran-3-ylphosphoramidochloridate 10 and of 135 mg (1.65 mmol) of N-methylimidazole in 20 mL of dry MeCN was refluxed for 48 h. The mixture was evaporated in vacuo, dissolved in 40 mL of DCM, washed twice with water, dried over $Na_2SO_4$ and evaporated in vacuo. The residue was dissolved in 1:1 $CHCl_3/Me_2CO$ mixture and filtered through 2 cm $SiO_2$ layer and evaporated in vacuo. It gave compound 1.10, LC-MS $[M+H]^+$ 799, which was hydrogenated in 25 mL of i-PrOH over 100 mg of 10% Pd/C. HPLC separation was carried out without acid and gave compound 1(14), LC-MS (ESI) $[M+H]^+$ 531, $^1H$ NMR (DMSO-$d_6$, 400 MHz) δ 7.48 (m, 1H), 7.39 (m, 4H), 7.23 (m, 3H), 6.43 (m, 1H), 6.14 (m, 2H), 5.75 (m, 1H), 4.35 (m, 3H), 4.19 (m, 1H), 4.05 (m, 1H), 2.33 (m, 1H), 1.85 (m, 1H), 1.35 (s, 3H), 1.31 (s, 3H).

EXAMPLE 5

(2R,3R,5R)-5-(4-amino-2-oxopyrimidin-1(2H)-yl)-4,4-difluoro-3-hydroxytetrahydrofuran-2-yl)methyl phenyl (S)-2-oxotetrahydrofuran-3-ylphosphoramidate 1.2(1). A solution of 2 g (2.6 mmol) of compound 1(5) was hydrogenated in 150 mL of isopropanol over 200 mg of 10% Pd/C. After the reaction was completed (LC-MS check) the mixture was filtered through celite, evaporated in vacuo and purified by column chromatography on $SiO_2$ (eluent MeCN: t-BuOH=5:1) that gave compound 1.2(1), LC-MS (ESI) $[M+H]^+$ 503, $^1H$ NMR (DMSO-$d_6$, 400 MHz) δ 7.44, 7.49 (2 d, J=7.6 Hz, 1H), 7.39 (m, 4H), 7.23 (m, 3H), 6.40, 6.44 (2 d, J=6.0 Hz, 1H), 6.14 (m, 2H), 5.73, 5.77 (2 d, J=7.6 Hz, 1H), 4.42 (m, 1H), 4.35 (m, 1H), 4.27 (m, 2H), 4.17 (m, 2H), 4.05 (m, 1H), 2.35 (m, 1H), 2.01 (m, 1H).

EXAMPLE 6

((2R,3R,5R)-5-(4-amino-2-oxopyrimidin-1(2H)-yl)-4,4-difluoro-3-hydroxytetrahydrofuran-2-yl)methyl phenyl 1-methyl-2-oxopyrrolidin-3-yl-phosphoramidate 1(13), its (S)-1(15) and (R)-isomer 2.2(1). A solution of compound 1(6) (108 mg, 0.14 mmol) was hydrogenated in 20 mL of dioxane over 100 mg of 10% Pd/C that gave compound 1(13), LC-MS (ESI) $[M+H]^+$ 516. $^1H$ NMR (DMSO-$d_6$, 400 MHz) δ 7.47 (m, 2H), 7.37 (m, 3H), 7.27 (m, 2H), 7.19 (m, 1H), 6.42 (m, 1H), 6.18 (m, 1H), 5.89 (m, 1H), 5.75 (m, 1H), 4.32 (m, 3H), 4.05 (m, 1H), 3.82 (m, 1H), 3.20 (m, 2H), 2.73 (s, 3H), 2.19 (m, 1H), 1.67 (m, 1H). HPLC separation without acid gave fast moving isomer, presumably (R)-isomer 2.2(1), LC-MS (ESI) $[M+H]^+$ 516, and slow moving isomer, presumably (S)-isomer 1(15), LC-MS (ESI) $[M+H]^+$ 516.

EXAMPLE 7

((2R,3R,5R)-5-(4-amino-2-oxopyrimidin-1(2H)-yl)-4,4-difluoro-3-hydroxytetrahydrofuran-2-yl)methyl phenyl 1-methyl-2-oxopiperidin-3-ylphosphoramidate 1(8).

A solution of compound 1(7) (194 mg, 0.24 mmol) was hydrogenated in 20 mL of ethanol over 100 mg of 10% Pd/C. HPLC separation without acid afforded compound 1(8). LC-MS (ESI) $[M+H]^+$ 530.

EXAMPLE 8

Preparation of a pharmaceutical composition in the form of tablet. Starch (1600 mg), ground lactose (1600 mg), talk (400 mg) and (2R,3R,5R)-5-(4-amino-2-oxopyrimidin-1(2H)-yl)-4,4-difluoro-2-((((S)-2-oxotetrahydrofuran-3-alamino)(phenoxy)phosphoryloxy)methyl)tetrahydrofuran-3-yl acetate 1.2(2) (1000 mg) were mixed together and pressed into bar. The resultant bar was comminuted into granules and sifted through sieve to collect granules of 14-16 mesh. The granules thus obtained were shaped into tablets of suitable form weighing 560 mg each.

EXAMPLE 9

Preparation of a pharmaceutical composition in the form of capsules. (2R,3R,5R)-5-(4-Amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2) and lactose powder were carefully mixed in ratio 2:1. The resultant powdery mixture was packed into gelatin capsules of suitable size by 300 mg to a capsule.

EXAMPLE 10

Preparation of a pharmaceutical composition in the form of compositions for intramuscular, intraperitoneal or hypodermic injections. (2R,3R,5R)-5-(4-amino-2-oxopyrimidin-1(2H)-yl)-4,4-difluoro-2-((((S)-2-oxotetrahydrofuran-3-ylamino)(phenoxy)phosphoryloxy)methyl)tetrahydrofuran-3-yl acetate 1.2(2) (500 mg), chlorobutanol (300 mg), propylene glycol (2 ml), and injectable water (100 ml) were mixed together. The resultant solution was filtered, placed into 1 ml ampoules and sealed.

EXAMPLE 11

A general protocol for the preparation of compounds of general formula 1, 1.1, and 1.2. The amine 3 (300 mg, 2.18 mmol) was mixed with a solution of aryl dichlorophosphate 4 (2.18 mmol) in dichloromethane (15 ml) and cooled to −70° C. under argon. A solution of triethylamine (0.6 ml, 4.36 mmol) in dichloromethane (3 mL) was added and the resulting mixture was stirred for 30 minutes at −70° C. After that the reaction mixture was warmed to room temperature and evaporated. The residue was mixed with ether, filtered and the precipitate formed was washed with ether. The filtrate was evaporated and the residue was subjected to chromatography on silica gel using ethyl acetate-hexane 1:1, 2:1 mixture as eluent. It gave aryl amidochlorophosphate 5. Aryl amidochlorophosphate 5 (2.9 mmol), substituted 1-((2R,4S,5R)-4-hydroxy-5-(hydroxymethyl)tetrahydrofuran-2-yl)pyrimidin-2,4(1H,3H)-dione (2.9 mmol) 6(1) or substituted 4-amino-1-((2R,4S,5R)-4-hydroxy-5-(hydroxymethyl)tetrahydrofuran-2-yl)pyrimidin-2(1H)-one (2.9 mmol) 6(2) and DBU (433 ml, 2.9 mmol) were dissolved in acetonitrile (20 ml), and the resultant mixture was refluxed for 16 hours. After cooling the reaction mixture was diluted with ethyl acetate and washed with water. The organic layer was dried over sodium sulfate and evaporated in vacuo. Purification of the product was carried out by HPLC method using mobile phase without acid. It gave compounds of the general formulas 1, 1.1 and 1.2, among them:

((2R,3R,5R)-5-(4-amino-2-oxopyrimidin-1(2H)-yl)-4,4-difluoro-3-hydroxytetrahydrofuran-2-yl)methyl p-tolyl (S)-2-oxo-tetrahydrofuran-3-yl-phosphoramidate 1(1), LCMS (ESI) [M+H]$^+$ 517;

((2R,3R,5R)-5-(4-amino-2-oxopyrimidin-1(2H)-yl)-4,4-difluoro-3-hydroxytetrahydrofuran-2-yl)methyl 4-chlorophenyl (S)-2-oxo-tetrahydrofuran-3-yl-phosphoramidate 1(2), LCMS (ESI) [M+H]$^+$ 537;

((2R,3R,5R)-5-(4-amino-2-oxopyrimidin-1(2H)-yl)-4,4-difluoro-3-hydroxytetrahydrofuran-2-yl)methyl 2,4-dichlorophenyl (S)-2-oxo-tetrahydrofuran-3-yl-phosphoramidate 1(3), LCMS (ESI) [M+H]$^+$ 572;

benzyl 1-((2R,4R,5R)-4-(benzyloxycarbonyloxy)-3,3-difluoro-5-(((S)—((S)-(2-oxotetrahydrofuran-3-ylamino)(phenoxy)phosphoryloxy)methyl)tetrahydrofuran-2-yl)-2-oxo-1,2-dihydropyrimidin-4-ylcarbamate 1(5), LCMS (ESI) [M+H]$^+$ 771. $^1$H NMR (DMSO-d$_6$, 400 MHz) δ 11.04 (s, 1H), 8.02 (d, J=7.6 Hz, 1H), 7.39 (m, 13H), 7.23 (m, 2H), 7.18 (m, 1H), 7.13 (d, J=7.2 Hz, 1H), 6.35 (t, J=8.6 Hz, 1H), 6.15 (dd, J$_1$=12.4 Hz, J$_2$=10.4 Hz, 1H), 5.38 (m, 1H), 5.24 (AB sys, J=12.0 Hz, 2H), 5.21 (s, 2H), 4.58 (m, 1H), 4.51 (m, 1H), 4.43 (m, 1H), 4.27 (m, 2H), 4.15 (m, 1H), 2.36 (m, 1H), 2.01 (m, 1H);

((2R,3R,5R)-5-(4-amino-2-oxopyrimidin-1(2H)-yl)-4,4-difluoro-3-hydroxytetrahydrofuran-2-yl)methyl phenyl 2-oxooxepan-3-ylphosphoramidate 1(9), LC-MS (ESI) [M+H]$^+$ 531;

((2R,3R,5R)-5-(2,4-dioxo-3,4-dihydropyrimidin-1(2H)-yl)-4,4-difluoro-3-hydroxytetrahydrofuran-2-yl)methyl phenyl 5,5-dimethyl-2-oxotetrahydrofuran-3-ylphosphoramidate 1(11), LCMS (ESI) [M+H]$^+$ 532;

((2R,3R,5R)-5-(2,4-dioxo-3,4-dihydropyrimidin-1(2H)-yl)-4,4-difluoro-3-hydroxytetrahydrofuran-2-yl)methyl phenyl 2-oxotetrahydrofuran-3-ylphosphoramidate 1.1(1), LCMS ESI) [M+H]$^+$ 504;

((2R,3R,4R,5R)-5-(2,4-dioxo-3,4-dihydropyrimidin-1(2H)-yl)-4-fluoro-3-hydroxy-4-methyltetrahydrofuran-2-yl)methyl phenyl (S)-2-oxotetrahydrofuran-3-ylphosphoramidate 1.1(2), LCMS (ESI) [M+H]$^+$ 500, $^1$H NMR (DMSO-d$_6$, 400 MHz) δ 11.47 (s, 1H), 7.55 (d, J=7.6 Hz, 1H), 7.39 (m, 2H), 7.26 (m, 2H), 7.19 (m, 1H), 6.13 (m, 1H), 6.03 (m, 1H), 5.89 (m, 1H), 5.58 (m, 1H), 4.30 (m, 5H), 4.05 (m, 1H), 3.83 (br m, 1H), 2.33 (m, 1H), 2.00 (m, 1H), 1.25 (m, 3H);

((2R,3R,5R)-3-(tert-butyldimethylsilyloxy)-5-(2,4-dioxo-3,4-dihydropyrimidin-1(2H)-yl)-4,4-difluorotetrahydrofuran-2-yl)methyl phenyl 1-methyl-2-oxopyrrolidin-3-ylphosphoramidate 1.1(4), LCMS (ESI) [M+H]$^+$ 631;

((2R,3R,5R)-5-(2,4-dioxo-3,4-dihydropyrimidin-1(2H)-yl)-4,4-difluoro-3-hydroxytetrahydrofuran-2-yl)methyl phenyl (R)-2-oxo-tetrahydrofuran-3-ylphosphoramidate 1.1(6), LCMS (ESI) [M+H]$^+$ 504, $^1$H NMR (DMSO-d$_6$, 400 MHz) δ 11.61 (s, 1H), 7.55 (m, 1H), 7.38 (m, 2H), 7.23 (m, 3H), 6.50 (br m, 1H), 6.13 (m, 2H), 5.65 (m, 1H), 4.25 (m, 7H), 2.34 (m, 1H), 2.00 (m, 1H);

(2R,3R,5R)-5-(4-amino-2-oxopyrimidin-1(2H)-yl)-4,4-difluoro-3-hydroxytetrahydrofuran-2-yl)methyl phenyl (S)-2-oxotetrahydrofuran-3-ylphosphoramidate 1.2(1), LCMS (ESI) [M+H]$^+$ 503, $^1$H NMR (DMSO-d$_6$, 400 MHz): δ 7.70 (d, J=7.2 Hz, 1H), 7.40 (m, 4H), 7.25 (m, 3H), 6.38 (m, 1H), 6.22 (m, 1H), 5.80 (d.d, J$_1$=7.6 Hz, J$_2$=2.8 Hz, 1H), 5.20 (b. s, 1H), 5.05 (m, 1H), 4.28 (m, 2H), 3.58-4.22 (m, 4H), 2.40 (m, 1H), 2.04 (m, 1H).

INDUSTRIAL APPLICABILITY

The invention could be used in medicine, veterinary, biochemistry.

The invention claimed is:

1. A compound selected from a (2R,3R,5R)-3-hydroxy-(5-pyrimidin-1-yl)tetrahydrofuran-2-yl)methyl aryl phosphoramidate of formula 1 or a (5)-(2R,3R,5R)-3-hydroxy-(5-pyrimidin-1-yl)tetrahydrofuran-2-yl)methyl aryl phosphoramidate of formula 2, or a pharmaceutically acceptable salt, a hydrate, a crystalline form or a stereoisomer thereof,

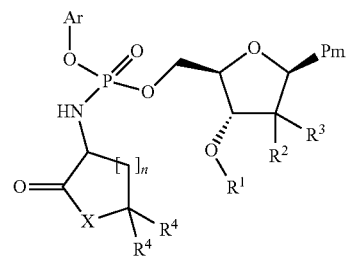

1

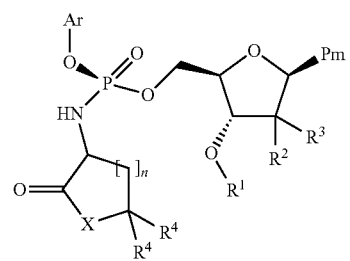

2 wherein:
R$^1$ is (i) hydrogen, (CH$_3$)$_2$[(CH$_3$)$_3$C]Si, a C$_2$-C$_6$acyl, optionally substituted with NR$^5$R$^6$ group, wherein R$^5$ and R$^6$ are independently hydrogen or a C$_1$-C$_4$ alkyl; or
(ii) 1-pyrrole-2-ylcarbonyl, piperidin-3-ylcarbonyl or piperidin-4-ylcarbonyl;
R$^2$ and R$^3$ are F; or R$^3$ is CH$_3$ and R$^2$ is F or OH;
R$^4$ is hydrogen or methyl;
Ar is a phenyl, a pyridyl or a naphthyl, wherein phenyl, pyridyl or naphthyl are optionally substituted with at least one of C$_{1-3}$ alkyl, C$_{2-4}$ alkenyl, C$_{2-4}$ alkynyl, C$_{1-3}$ alkoxy, F, Cl, Br, I, nitro, cyano, or —N(C$_{1-3}$ alkyl)$_2$;
Pm is 2,4-dioxo-3,4-dihydro-2H-pyrimidin-1-yl or 4-(4-amino-2-oxo-2H-pyrimidin-1-yl), in which amino group is optionally substituted with 1-pyrrole-2-ylcarbonyl, piperidin-3-ylcarbonyl, piperidin-4-ylcarbonyl or radical C(O)R⁸, wherein R⁸ is (i) a $C_1$-$C_4$alkyl, optionally substituted with NR⁶R⁷ group, wherein R⁶ and R⁷ are independently hydrogen or $C_1$-$C_4$ alkyl; or (ii) a $C_{1-3}$ alkoxy optionally substituted with a phenyl;

X is O or N—R⁹, wherein R⁹ is a $C_1$-$C_4$alkyl, optionally substituted with OH or $OCH_3$;

n=1, 2 or 3.

2. The compound of claim 1 of formula 1.1 or formula 2.1, or a pharmaceutically acceptable salt, a hydrate, a crystalline form or a stereoisomer thereof,

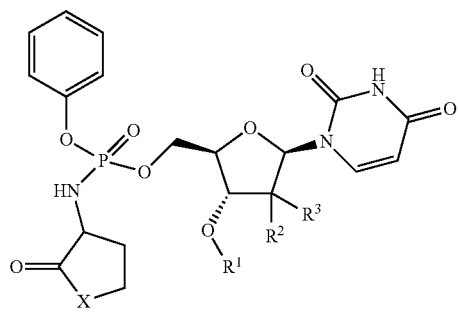

1.1

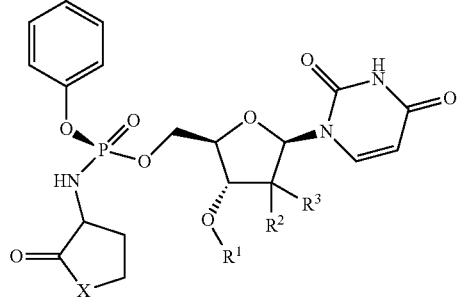

2.1 wherein R¹, R², R³, and X are as defined herein above.

3. The compound of claim 1 of formula 1.2 or formula 2.2, or a pharmaceutically acceptable salt, a hydrate, a crystalline form or a stereoisomer thereof,

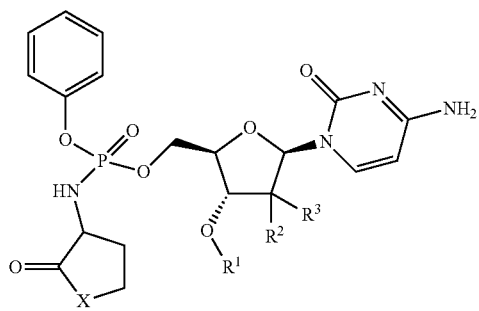

1.2

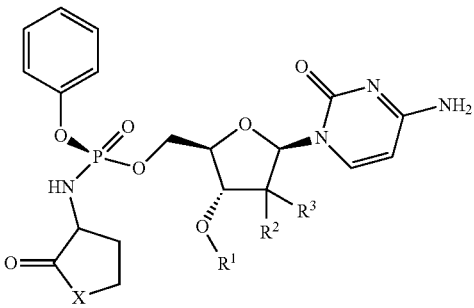

2.2 wherein R¹, R², R³, and X are as defined herein above.

4. The compound of claim 1 selected from the group consisting of:

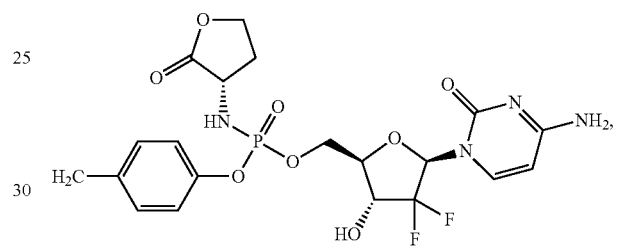

(1)1

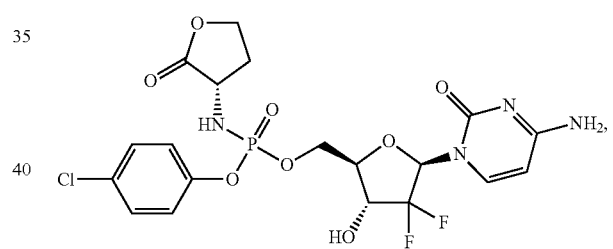

1(2)

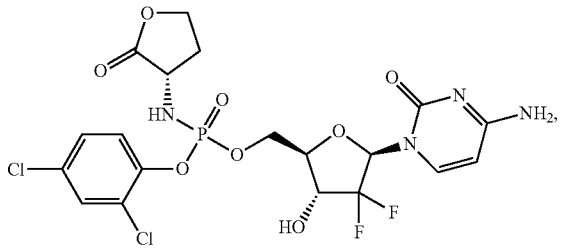

1(3)

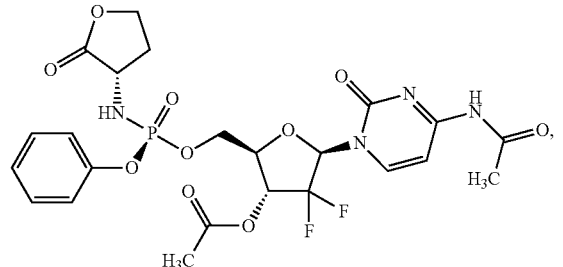

1(4)

1(5)
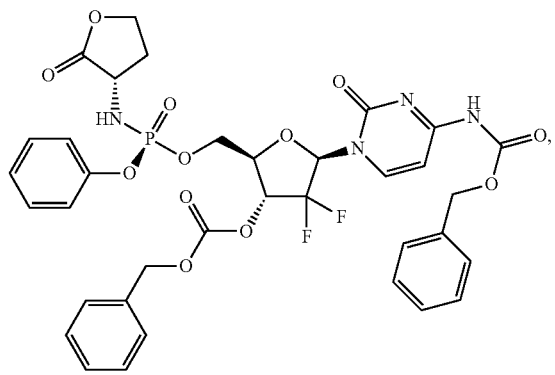
1(6)
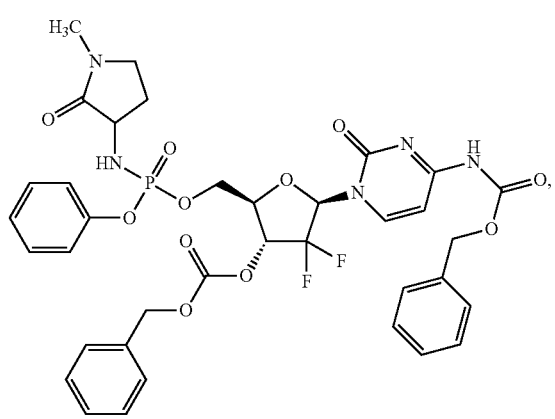
1(7)
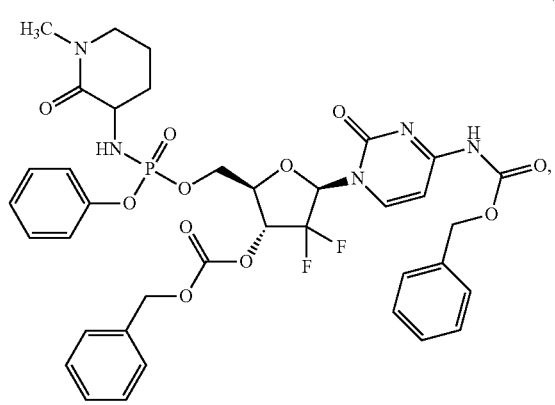
1(8)
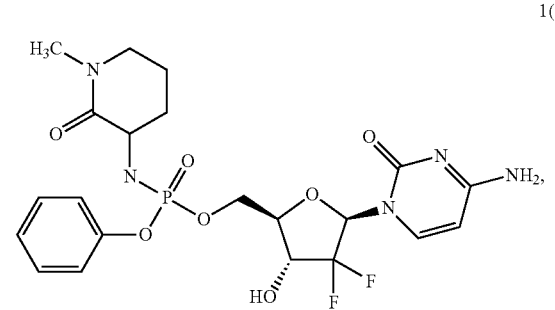
1(9)
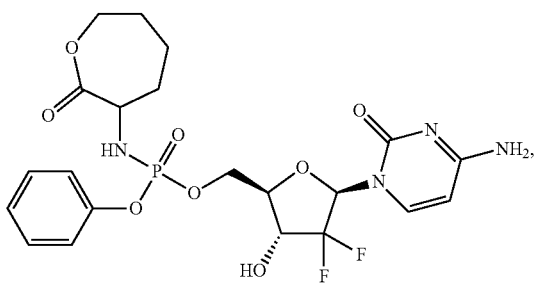
1(10)
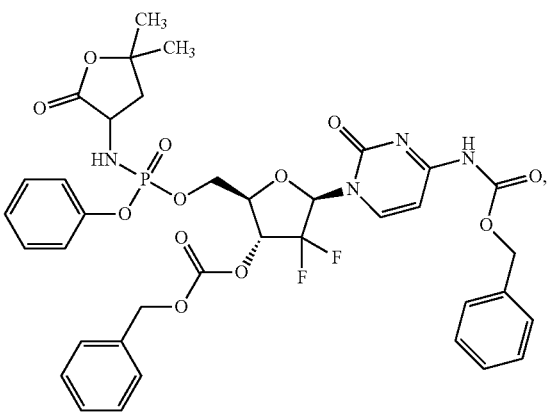
1(11)
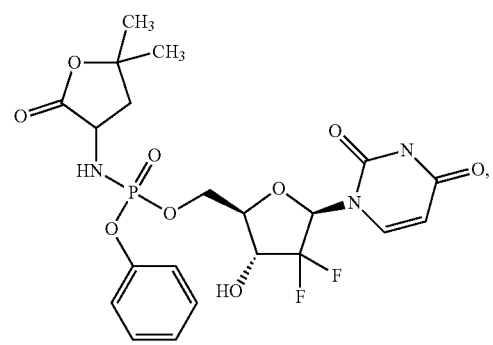
1(12)
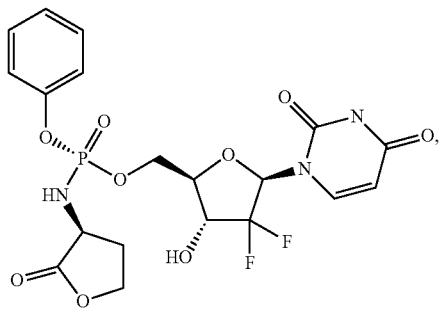

1(13)
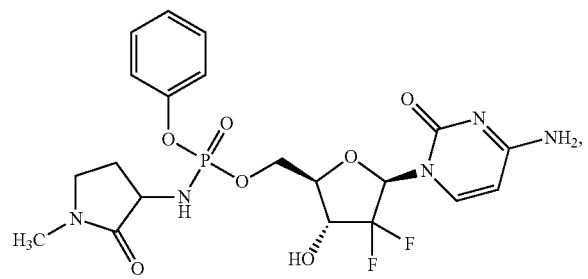
1(14)
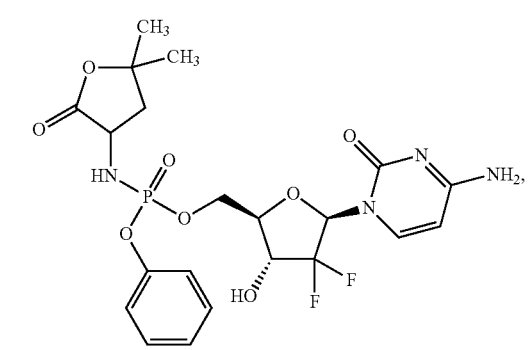
1(15)
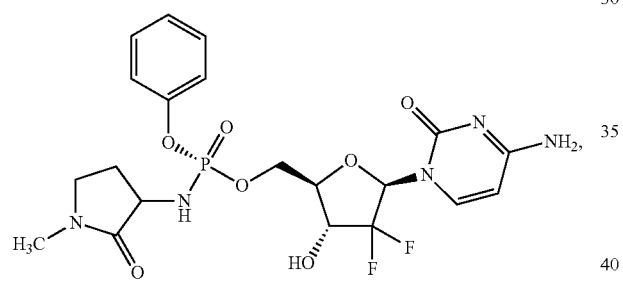
1.1(1)
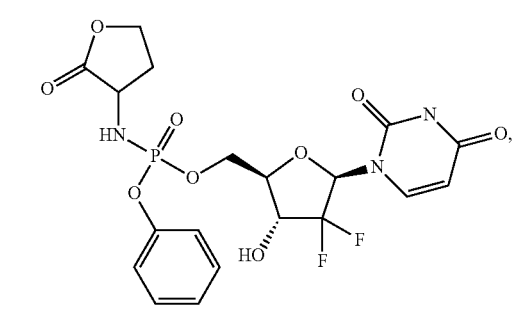
1.1(2)
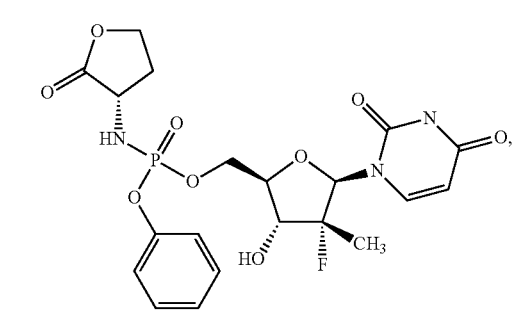
1.1(3)
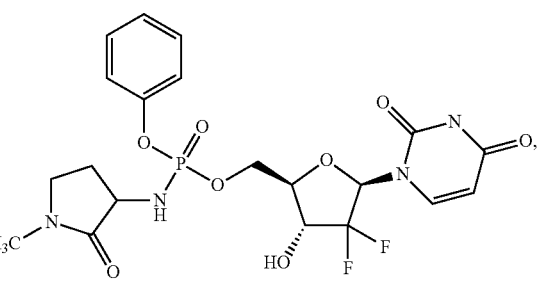
1.1(4)
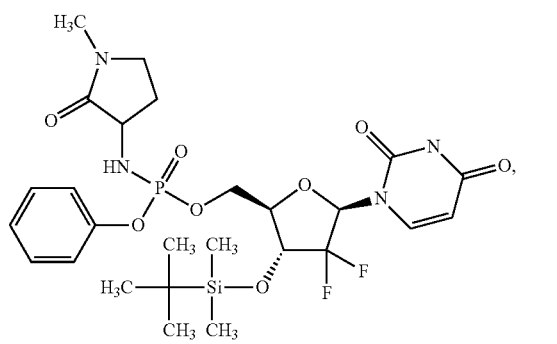
1.1(5)
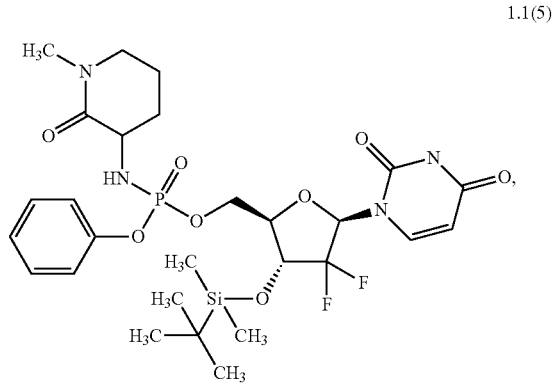
1.1(6)
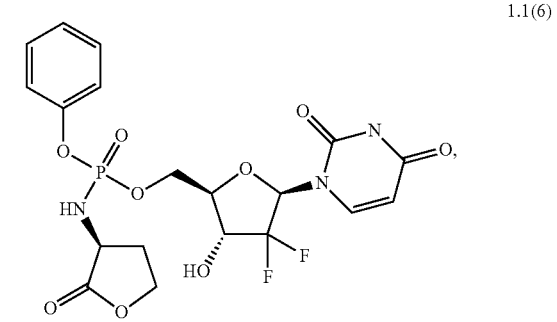

1.2(1)
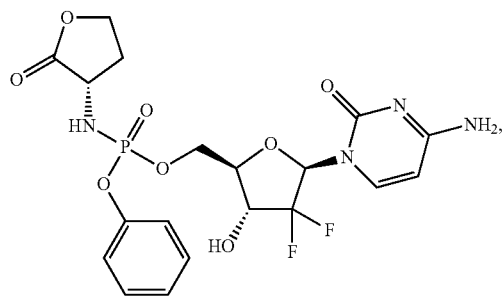
1.2(2)
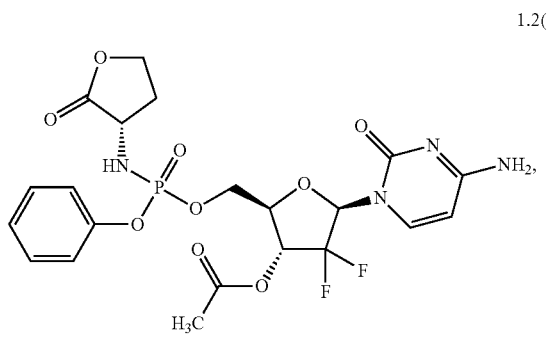
1.2(3)
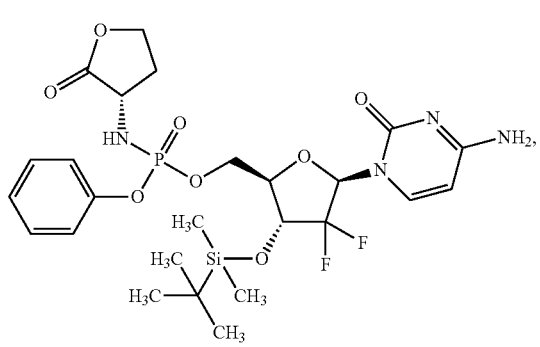
1.2(4)
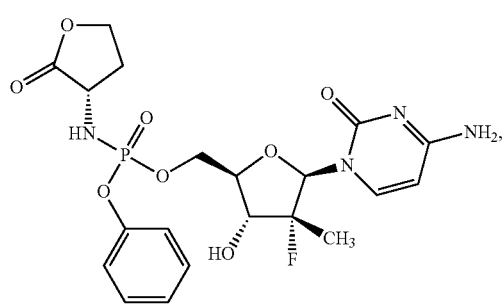
1.2(5)
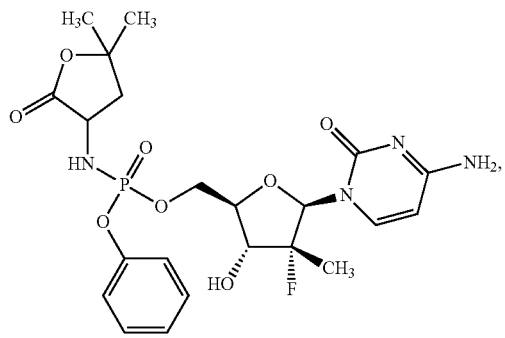
1.2(6)
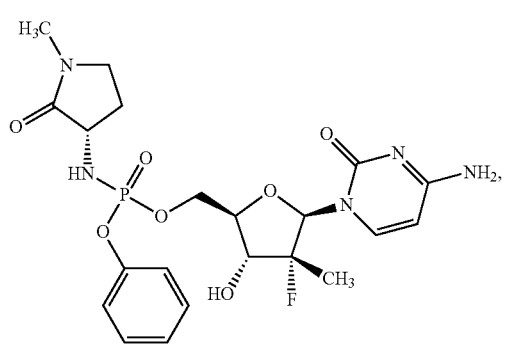
2.1(1)
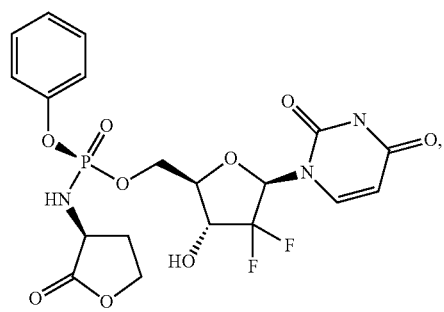
2.1(2)
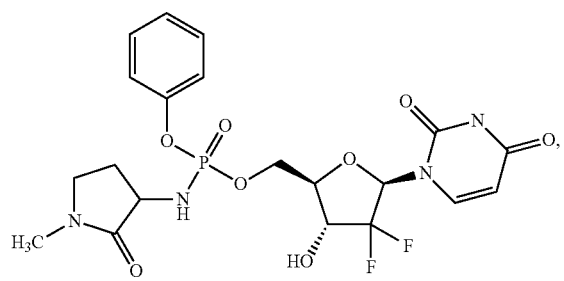
and 2.2(1)

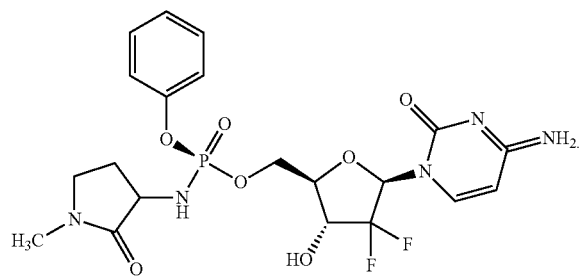

6

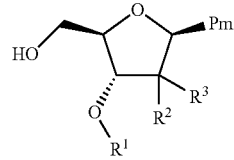

wherein Ar, n, $R^1$, $R^2$, $R^3$, $R^4$, and Pm are defined as above.

9. A method for the preparation of a compound of formula 1, 1.1, or 1.2, or a stereoisomer thereof, comprising interacting a compound of formula 4 with a compound of formula 6 and subsequently mixing with an amine of formula 8, 5. A pharmaceutical composition comprising a compound of formula 1 or formula 2, or a pharmaceutically acceptable salt, a hydrate, a crystalline form or a stereoisomer thereof, according to claim 1 in a therapeutically effective amount and at least one pharmaceutically acceptable excipient.

6. The pharmaceutical composition of claim 5 in the form of a tablet, a capsule, an injection, a liniment, a rectal gel, or a rectal suspension placed in a pharmaceutically acceptable packing.

7. The pharmaceutical composition of claim 5 further comprising a drug substance selected from the group consisting of: an inosine 5 monophosphate dehydrogenase inhibitor, HCV protease NS3 inhibitor, HCV protease NS3/4A inhibitor, and RNA polymerase NS5A inhibitor.

8. A method for the preparation of a compound of formula 1, 1.1, or 1.2, or a stereoisomer thereof, comprising interacting an amine of formula 3 with a compound of formula 4 and subsequently mixing with a compound of formula 6,

4

ArOPOCl$_2$

6

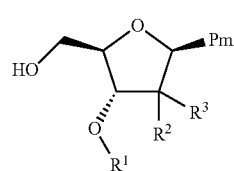

8

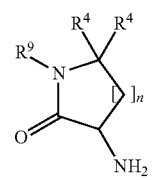

wherein Ar, n, $R^1$, $R^2$, $R^3$, $R^4$, $R^9$, and Pm are defined as above.

10. The method of claim 9 for the preparation of a compound of formula 1, 1.1, or 1.2, wherein $R^1$ is acyl, or a stereoisomer thereof, comprising acidifying a compound of formula 1, wherein $R^1$ is hydrogen.

11. The method of claim 9 for the preparation of a compound of formula 1, 1.1, or 1.2, wherein $R^1$ is dimethyl-tert-butylsilyl, or a stereoisomer thereof, comprising mixing a dimethyl-tert-butylsilyl chloride with a compound of formula 1, wherein $R^1$ is hydrogen.

3

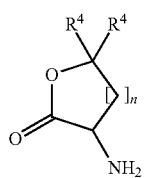

4

ArOPOCl$_2$

\* \* \* \* \*